US011975033B2

(12) United States Patent
Abbott

(10) Patent No.: US 11,975,033 B2
(45) **Date of Patent: *May 7, 2024**

(54) GENE EXPRESSION SYSTEM FOR PROBIOTIC MICROORGANISMS

(71) Applicant: ZBiotics Company, San Francisco, CA (US)

(72) Inventor: Zachary Abbott, Millbrae, CA (US)

(73) Assignee: ZBiotics Company, San Francisco, CA (US)

(*) Notice: Subject to any disclaimer, the term of this patent is extended or adjusted under 35 U.S.C. 154(b) by 643 days.

This patent is subject to a terminal disclaimer.

(21) Appl. No.: 17/080,185

(22) Filed: Oct. 26, 2020

(65) Prior Publication Data

US 2021/0121506 A1 Apr. 29, 2021

Related U.S. Application Data

(63) Continuation of application No. 16/048,147, filed on Jul. 27, 2018, now Pat. No. 10,849,938.

(60) Provisional application No. 62/558,346, filed on Sep. 13, 2017.

(51) Int. Cl.

| | |
|---|---|
| ***A61K 35/742*** | (2015.01) |
| ***A61K 9/00*** | (2006.01) |
| ***A61P 39/02*** | (2006.01) |
| ***C07K 14/32*** | (2006.01) |
| ***C12N 9/02*** | (2006.01) |
| ***C12N 15/63*** | (2006.01) |
| *A61K 35/00* | (2006.01) |
| *A61K 35/741* | (2015.01) |
| *A61K 38/00* | (2006.01) |

(52) U.S. Cl.

CPC .......... *A61K 35/742* (2013.01); *A61K 9/0053* (2013.01); *A61P 39/02* (2018.01); *C07K 14/32* (2013.01); *C12N 9/0008* (2013.01); *C12N 15/63* (2013.01); *C12Y 102/01003* (2013.01); *A61K 9/0095* (2013.01); *A61K 2035/115* (2013.01); *A61K 35/741* (2013.01); *A61K 38/00* (2013.01)

(58) Field of Classification Search

CPC .. A61K 35/742; A61K 9/0053; A61K 9/0095; A61K 35/741; A61K 38/00; A61K 2035/115; A61P 39/02; C07K 14/32; C12N 9/0008; C12N 15/63; C12Y 102/01003

See application file for complete search history.

(56) References Cited

U.S. PATENT DOCUMENTS

| | | | |
|---|---|---|---|
| 4,801,536 | A | 1/1989 | Stahl et al. |
| 5,160,742 | A | 11/1992 | Mazer et al. |
| 5,275,819 | A | 1/1994 | Amer et al. |
| 5,527,784 | A | 6/1996 | Ishihara |
| 5,800,821 | A | 9/1998 | Acheson et al. |
| 7,888,064 | B2 | 2/2011 | Berger et al. |
| 9,161,957 | B2 | 10/2015 | Smith et al. |
| 9,630,997 | B2 | 4/2017 | Hughes et al. |
| 9,782,351 | B2 | 10/2017 | Gill et al. |
| 9,987,224 | B2 | 6/2018 | Kovarik et al. |
| 10,548,844 | B2 | 2/2020 | Anselmo et al. |
| 10,849,938 | B2 | 12/2020 | Abbott |
| 11,696,932 | B2 | 7/2023 | Abbott |
| 2003/0031659 | A1 | 2/2003 | Farmer |
| 2007/0161031 | A1 | 7/2007 | Trinklein et al. |
| 2009/0060894 | A1 | 3/2009 | Somberg et al. |
| 2010/0113423 | A1 | 5/2010 | Mochly-Rosen et al. |
| 2010/0285532 | A1 | 11/2010 | Berger et al. |
| 2012/0034322 | A1 | 2/2012 | Oda et al. |
| 2013/0004475 | A1 | 1/2013 | Hatanaka et al. |
| 2013/0089535 | A1 | 4/2013 | Yamashiro et al. |
| 2014/0065697 | A1 | 3/2014 | Zhang et al. |
| 2014/0134700 | A1 | 5/2014 | Lu et al. |
| 2014/0186436 | A1 | 7/2014 | Yang et al. |
| 2015/0087702 | A1 | 3/2015 | Talalay et al. |
| 2016/0074445 | A1 | 3/2016 | Smith et al. |
| 2016/0340665 | A1 | 11/2016 | Falb et al. |

(Continued)

FOREIGN PATENT DOCUMENTS

| | | | |
|---|---|---|---|
| CN | 101649323 | A | 2/2010 |
| CN | 101985625 | A | 3/2011 |

(Continued)

OTHER PUBLICATIONS

Konkit et al. Aldehyde dehydrogenase activity in Lactococcus chungangensis: Application in cream cheese to reduce aldehyde in alcohol metabolism. J. Dairy Sci. 2016; 99:1755-1761. (Year: 2016).*

(Continued)

*Primary Examiner* — Arthur S Leonard

*Assistant Examiner* — Jianjian Zhu

(74) *Attorney, Agent, or Firm* — Choate, Hall & Stewart LLP; Nnamdi Edokobi; Brenda Herschbach Jarrell

(57) ABSTRACT

Provided herein are recombinant microorganisms that express a subject polypeptide. Microorganisms can comprise an expression construct comprising a flagellin promoter operatively linked with a heterologous nucleotide sequence encoding the subject polypeptide. The flagellin promoter sequence can comprise a genetic modification that reduces CsrA inhibition of translation. Microorganisms also can comprise a genetic modification that reduces FlgM inhibition of SigD initiation of transcription. The target polypeptide can be an aldehyde dehydrogenase. Such microorganisms are useful in the treatment of alcohol hangover.

16 Claims, 6 Drawing Sheets

Specification includes a Sequence Listing.

(56) References Cited

U.S. PATENT DOCUMENTS

| | | | |
|---|---|---|---|
| 2017/0319636 | A1 | 11/2017 | Kim et al. |
| 2018/0333441 | A1 | 11/2018 | Chung |
| 2019/0224111 | A1 | 7/2019 | Bianco-Peled et al. |
| 2020/0345793 | A1 | 11/2020 | Abbott |

FOREIGN PATENT DOCUMENTS

| | | | |
|---|---|---|---|
| CN | 102337280 | A | 2/2012 |
| CN | 103114056 | A | 5/2013 |
| CN | 106222190 | A | 12/2016 |
| CN | 106867930 | A | 6/2017 |
| CN | 107815458 | A | 3/2018 |
| CN | 108103081 | A | 6/2018 |
| EP | 2235045 | B1 | 10/2012 |
| JP | H09168391 | A | 6/1997 |
| JP | 2660520 | B2 | 10/1997 |
| JP | 2013-066446 | A | 4/2013 |
| JP | 2014-506466 | A | 3/2014 |
| JP | 5881352 | B2 | 3/2016 |
| KR | 10-2013-0092182 | A | 8/2013 |
| KR | 2013-0092182 | A | 8/2013 |
| KR | 101853603 | B1 | 5/2018 |
| WO | WO-1987/002385 | A1 | 4/1987 |
| WO | WO-1989/010967 | A1 | 11/1989 |
| WO | WO-2006/032693 | A1 | 3/2006 |
| WO | WO-2015/023989 | A1 | 2/2015 |
| WO | WO-2016/172341 | A2 | 10/2016 |
| WO | WO-2016/201380 | A8 | 1/2017 |
| WO | WO-2019/055707 | A1 | 3/2019 |

OTHER PUBLICATIONS

Amidon, S., et. al., Colon-Targeted Oral Drug Delivery Systems: Design Trends and Approaches, AAPS PharmSciTech, 16(4): 731-741, (2015).

Ben-Yehuda, S., D.Z. Rudner, and R. Losick, RacA, a bacterial protein that anchors chromosomes lo the cell poles. Science, 299(5606):532-6, (2003).

Calvo, R.A., and Kearns, D.B., FIgM Is Secreted by the Flagellar Export Apparatus in Bacillus subtilis, 197(1):81-91, (2015).

Caramori, T., el al., Role of FIgM in sigma D-dependent gene expression in Bacillus subtilis. J Bacteriol., 178 (11):3113-8, (1996).

Casula, G. and Cutting, S., Bacillus Probiotics: Spore Germination in the Gastrointestinal Tract, 68(5):2344-2352, (2002).

Chen, R., el al., Role of the sigmaD-dependent autolysins in Bacillus subtilis population heterogeneity. J Bacterial, 191(18):5775-84, (2009).

Cross, R. The world's first GMO probiotic is for sale; it's designed to prevent hangovers, pp. 1-4, (2019).

Cutting, S.M., et. al., Oral Vaccine Delivery by Recombinant Spore Probiotics, 28(6):487-505, (2009).

Dominguez Rubio, A.P. et al., Transcytosis of Bacillus subtilis extracellulas vesicles through an in vitro intestinal epithelial cell model, Scientific Reports, 10:3120, (2020).

Duc, L.H., et. al., Germination of the Spore in the Gastrointestinal Tract Provides a Novel Route for Heterologous Antigen Delivery, 21(27-30):4215-24, (2003).

Elshaghabee, F.M., et al., Bacillus As Potential Probiotics: Status, Concerns, and Future Perspectives, Frontiers in Microbiology, 8(1490):1-15, (2017).

Gibson, D.G., et al., Enzymatic assembly of DNA molecules up to several hundred kilobases. Nat Methods, 6(5):343-5, (2009).

Gold et al., Cloning and Expression of the Zymomonas mobilis "Production of Ethanol" Genes in Lactobacillus casei. Current Microbiology, 33:256-260, (1996).

Guttenplan, S.B., S. Shaw, and D.B. Kearns, The cell biology of peritrichous flagellin Bacillus subtilis. Mol Microbiol, 87(1):211-29.[000153] 4, (2013). Macnab, R.M., Genetics and biogenesis of bacterial flagella. Annu Rev Genet, 26:131-58 (1992).

Ho, K.K. and H. Weiner. Isolation and characterization of an aldehyde dehydrogenase encoded by the aldB gene o1 *scherichia coli*. J Bacterial, 187(3):1067-73, (2005).

Homann et al., Microbially produced acetaldehyde from ethanol may increase the risk of colon cancer via folate eficiency, Int. J. Cancer, 86:169-173 (2000).

Hong, H.A., et. al., The use of bacterial spore formers as probiotics, FEMS Microbiology reviews, pp. 813-835, (2005).

Hosoi, T., et al., [Abstract only], Changes in Fecal Microflora Induced by Intubation of Mice with Bacillus Subtilis (Natto) Spores are Dependent upon Dietary Components, Can J Microbiol., 45(1):59-66, (1999).

Hosseini, S. et. al., Biological Containment of Genetically Modified Bacillus subtilis, Applied and Environmental Microbiology, 84(3):1-15, (2018).

Howland, et al, Are Some Drinkers Resistant to Hangover? A Literature Review, Current Drug abuse Reviews, Bentham Science Publishers Ltd., 1:42-46, (2008).

ISA/US, International Search Report and Written Opinion for PCT/2018/050957, dated Feb. 5, 2019, 17 pages.

ISA/US, International Searching Authority Invitation to Pay Additional Fees and Where Applicable, Protest Fee for CT/US2018/050957, dated Nov. 30, 2018.

Jendrossek, D., A. Steinbuchel, and H.G. Schlegel, Three different proteins exhibiting NAO-dependent cetaldehyde dehydrogenase activity from Alcaligenes eutrophus. Eur J Biochem, 167(3):541-8, (1987).

Jokelainen et al., In vitro acetaldehyde formation by human colonic bacteria, Gut, 35:1271-1274, (1994).

Kullen et al., Genetic Modification of Intestinal Lactobacilli and Bifidobacteria. Curr. Issues Mol. Biol., 2(2):41-50, (2000).

Leser, T.D., et al., Germination and outgrowth of Bacillus subtilis and Bacillus licheniformis spores in the gastrointestinal tract of pigs, Journal of Applied Microbiology, 104(2008):1025-1033, (2007).

Lu, J. et. al., Alleviating acute alcoholic liver injury in mice with Bacillus subtilis co-expressing alcohol dehydrogenase and acetaldehyde dehydrogenase, Journal of Functional Foods, 49:342-350, (2018).

Lucchetti-Miganeh, C. et. al., The post-transcriptional regulator CsrA plays a central role in the adaptation of bacterial pathogens to different stages of infection in animal hosts, 154:16-29, (2008).

Lyu Y. et al. Heterologous Expression of Aldehyde Dehydrogenase in Lactococcus lactis for Acetaldehyde Detoxification at Low pH, 184(2): 570-581, (2017).

MacNab, RM., Genetics and biogenesis of bacterial flagella. Annu Rev Genet, 26:131-58, (1992).

Mukherjee, S. and D.B. Kearns, The structure and regulation offlagellin Bacillus subtilis. Annu Rev Genet, 8:319-40, (2014).

Mukherjee, S., et al., CsrA-FliW interaction governs flagellin homeostasis and a checkpoint on flagellar morphogenesis in Bacillus subtilis_ Mol Microbial, 82(2):447-61, (2011).

Nosova, T., et. al., Acetaldehyde Production and Metabolism by Human Indigenous and Probiotic Lactobacillus and Bifidobacterium Strains, 35(6):561-568, (2000).

Olmos, J. and Paniagua-Michel, J., Bacillus subtilis A Potential Probiotic Bacterium to Formulate Functional Feeds for Aquaculture, Journal of Microbial & Biochemical Technology, 6(7): 361-365, (2014).

Oshiro, S. et. al., Robust Stoichiometry of FliW-CsrA Governs Flagellin Homeostasis and Cytoplasmic Organization in Bacillus subtilis, 10(3):1-19, (2019).

Rodriguez-Zavala, J. et al., Characterization of *E.coli* tetrameric aldehyde dehydrogenases with atypical properties compared to other aldehyde dehydrogenases. Protein Science, 15:1387-1396. (2006).

Roshni Amalaradjou, M.A. and Bhunia, A.K., Bioengineered probiotics, a strategis approach to control enteric infections, Bioengineered, 4(6): 379-387, (2013).

Salaspuro, M., Microbial metabolism of ethanol and acetaldehyde and clinical consequences. Addict Biol, 2(1):35-46, (1997).

Schmidt, K., et. al., Prebiotic intake reduces the waking cortisol response and alters emotional bias in healthy volunteers, Psychopharmacology, 232(10):1793-801, (2015).

(56) References Cited

OTHER PUBLICATIONS

Sorokulova, I., Modern Status and Perspectives of Bacillus Bacteria as Probiotics, Journal of Probiotics and Health, 1(4):2-5, (2013).
Sprince, H., et al. [Abstract only], Protective action of ascorbic acid and sulfur compounds against acetaldehyde toxicity: implications in alcoholism and smoking, Agents Actions, 5(2):164-173, (1975).
Suva, M., et. al., Novel insight on probiotic Bacillus subtilis: Mechanism of action and clinical applications, Journal of Current Research in Scientific Medicine, 2(2):65-72, (2016).
Szmigiel, I., et. al., The influence of Bacillus subtilis 87Y isolated from Eisenia fetida on the growth of pathogenic and probiotic microorganisms, (2019).
Tam, N.K.M., et al., The Intestinal Life Cycle of Bacillus subtilis and Close Relatives, Journal of Bacteriology, 188(7): 2692-2700, (2006).
Vakulskas, C.A., et al., Regulation of bacterial virulence by Csr (Rsm) systems. Microbial Mal Biol Rev, 79(2):193-224, (2015).
Vogt, C.M., et al., Mouse intestinal microbiota reduction favors local intestinal immunity triggered by antigens displayed in Bacillus subtilis biofilm, Microbial Cell Factories, 17:187, (2018).
Wall, et al., Hangover Symptoms in Asian Americans with Variations in the Aldehyde Dehydrogenase (ALDH2) Gene, Journal of Studies on Alchol, 61(1):13, 7 pages, (2000).
www.alcohol.org/bac-calculator, pp. 1-2, (2019).
Yakhnin, H., et al., CsrA of Bacillus subtilis regulates translation initiation of the gene encoding the flagellin protein (hag) by blocking ribosome binding. Mol Microbiol, 64(6):1605-1620 (2007).
Yao et al., Acetaldehyde Detoxification Using Resting Cells of Recombinant *Escherichia coli* Overexpressing Acetaldehyde Dehydrogenase. Appl Biochem Biotechnol, 172:2030-2040, (2014).
Yurina, V., Live Bacterial Vectors—A Promising DNA Vaccine Delivery System, Med Sci (Basel), 6(2):1-16, (2018).
Zhu, et al., Isolation of strong constitutive promoters from *Lactococcus lactis* subsp. lactis NB. FEMS Microbiology _Letters, 362(16):1-6, (2015).
Li, F. et. al., Probiotics and alcoholic liver disease: Treatment and Potential Mechanisms, Gastroenterology research and Practice, 2016(1): 1-11, (2016).
Schräder, T., et. al., NAD(P)-Dependent aldehyde dehydrogenases induced during growth of Ralstonia eutropha Strain Bo on Tetrahydrofurfuryl alcohol, Journal of Bacteriology, 183(24):7408-7411, (2001).
Wang, F., et. al., Effects of beverages on alcohol metabolism: Potential health benefits and harmful impacts, International Journal of Molecular Sciences, 17(354):1-12, (2016).
Koo, O.K. et al., Cloning and characterization of the bifunctional alcohol/acetaldehyde dehydrogenase gene (adhE) in Leuconostoc mesenteroides isolated from kimchi, Biotechnol. Lett., 27(7):505-510 (2005).

* cited by examiner

FIG. 4.

-182 ggaattgacgccccaaagcatattgatattcacaggaaagaaatttact tgaccattcaggaagaaaataaccgtgcagcagcgttatccagcgatgt gatctccgcattatcctcacaaaaaagtgaggatttttttatttttgt

-35 -10 +1 attaacaaaatcagagacaatccgatattaatgatgtagccgggaggag gcgcaaaagactcagccagttacaaaataagggcacaaggacgtgcctt CsrA BS1 aacaacatattcagggaggaacaaaacaATG

CsrA BS2

GENE EXPRESSION SYSTEM FOR PROBIOTIC MICROORGANISMS

REFERENCE TO RELATED APPLICATIONS

This application is a continuation of U.S. application Ser. No. 16/048,147, filed Jul. 27, 2018, and claims the benefit of the priority date of U.S. Provisional Application No. 62/558,346, filed Sep. 13, 2017, each of which is incorporated herein by reference in its entirety.

STATEMENT AS TO FEDERALLY SPONSORED RESEARCH

None.

SEQUENCE LISTING

The instant application contains a Sequence Listing which has been submitted electronically in ASCII format and is hereby incorporated by reference in its entirety. Said ASCII copy, created on Oct. 26, 2020, is named 2013694_0015 Sequence_Listing and is 29,350 bytes in size.

BACKGROUND

When one consumes alcohol, the major pathway for its removal from the bloodstream is via oxidation in the liver to acetaldehyde via alcohol dehydrogenase enzymes. Acetaldehyde is subsequently oxidized in the liver to acetate via acetaldehyde dehydrogenase enzymes. When alcohol is consumed in large quantities and/or at a fast rate, the highly toxic intermediary acetaldehyde can accumulate and subsequently be released back into the bloodstream, where—abetted by its high solubility—it can act throughout the body. Not only is acetaldehyde a known carcinogen, its toxic effects are a well-studied and documented cause of many of the effects of an alcohol hangover. Indeed, removing acetaldehyde has been demonstrated to reduce hangover symptoms. PMID: 16554376 (PubMed ID). Conversely, when the body's ability to oxidize acetaldehyde to acetate is inhibited either chemically (e.g. with disulfiram) or genetically (e.g., single nucleotide polymorphisms in acetaldehyde dehydrogenase genes common in East Asian populations), extremely amplified hangover symptoms are experienced.

There have been several previous attempts to reduce, eliminate, or prevent the effects of a hangover. Some have attempted to enzymatically or otherwise reduce the amount of ethanol absorbed or increase the rate of ethanol removal from the body (patent publication US2009-0060894A1). However, these methods have at least two potential pitfalls: (1) their methods of action effect the consumer's blood alcohol content itself, which may be undesirable; and (2) accelerated ethanol metabolism into acetaldehyde could increase the body's exposure to acetaldehyde and exacerbate symptoms and/or merely induce hangover symptoms earlier rather than preventing them. In short, ethanol-centered strategies do not directly address the problem of acetaldehyde toxicity.

More directly, other groups have attempted to address acetaldehyde itself. US patent publication 2013-0089535A1 used enzyme preparations in the oral cavity. While there is evidence that alcohol consumption does raise the acetaldehyde concentration in saliva, it is unlikely that acetaldehyde removed from the oral cavity would have any significant effect on the systemic acetaldehyde toxicity responsible for an alcohol hangover.

Sprince, H., et al. (*Protective action of ascorbic acid and sulfur compounds against acetaldehyde toxicity: implications in alcoholism and smoking*. Agents Actions, 1975. 5(2): p. 164-73) refers to using small molecules to bind and remove acetaldehyde [1].

US patent publication 2015-0087702A1 refers to using small molecules increase the rate or expression of human enzymes to remove acetaldehyde.

Other groups have developed expression systems based on *Bacillus* or other bacterial flagellar regulatory regions (U.S. Pat. No. 7,888,064B2, European patent EP2235045B1), or by manipulating specifically flgM and CsrA (Japanese patent JP5881352B2).

Liu, Y. et al. ("Heterologous Expression of Aldehyde Dehydrogenase in *Lactococcus lactis* for Acetaldehyde Detoxification at Low pH", *Appl Biochem Biotechnol.* 8 Aug. 2017) refers to application of *Lactococcus lactis* with the NIsin Controlled Expression (NICE) System to express the aldehyde dehydrogenase gene (istALDH) in order to catalyze oxidation of acetaldehyde at low pH.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

*subtilis* expressing AldB under pHyspank promoter. Lanes 4 and 5 are uninduced and induced cultures (respectively) of *B. subtilis* expressing AcoD under pHyspank promoter. Lane 6 is a culture of *B. subtilis* with flgM deleted but hag still intact (negative control for heterologous protein expression). Lane 7 is a culture of *B. subtilis* expressing GFP (protein band of interest indicated by arrowhead) under the modified hag promoter. Lanes 8, 9, and 10 are cultures of *B. subtilis* expressing n-terminal 6×-histidine-tagged AcoD ("6×-histidine" disclosed as SEQ ID NO: 22), untagged AcoD, and n-terminal 6×-histidine-tagged AldB ("6×-histidine" disclosed as SEQ ID NO: 22) (respectively; protein band of interest indicated by arrowhead) under the modified hag promoter.

FIG. 4 shows a promoter structure for hag gene [SEQ ID NO: 7]. Identified in the figure are: the promoter start position (indicated by arrow and "−182"), the SigD RNA polymerase binding site (underlined and labelled "−10" and "−35"), the transcriptional start site (indicated by arrow and "+1"), CsrA binding sites 1 and 2 (bracketed and labeled "CsrA BS1/2"), the residue targeted for G-to-A point mutation to prevent CsrA binding as discussed in methods (circled "g"), and the Shine-Dalgarno sequence (boxed). ATG (capitalized in sequence) is the start codon for hag protein or any heterologous polypeptide.

Figure 5:
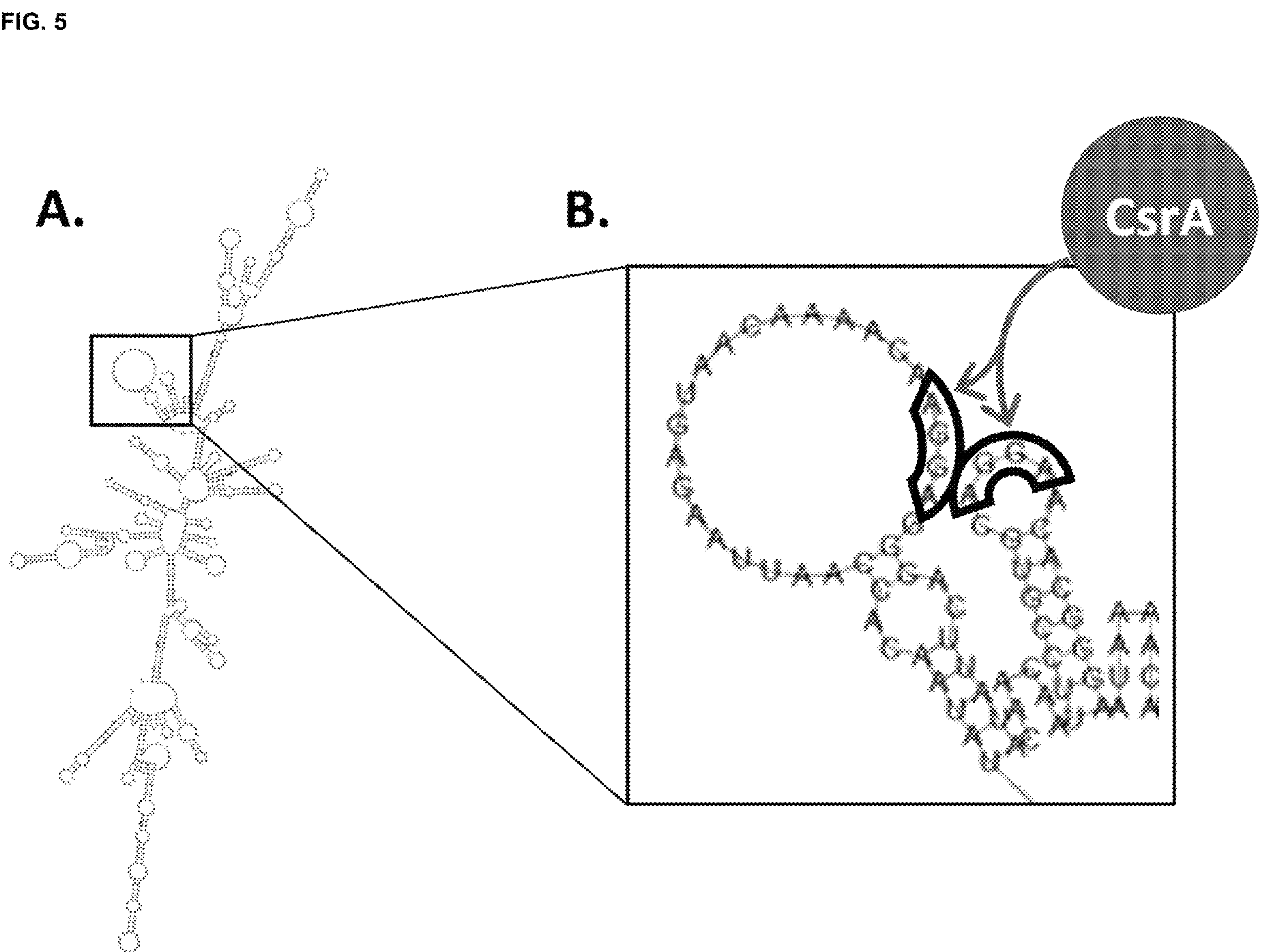

FIG. 5 shows predicted secondary structure of hag mRNA [SEQ ID NO: 21], including 5'-UTR (fold prediction generated by University of Vienna's RNA fold software; citation: Gruber A R, Lorenz R, Bernhart S H, Neuböck R, Hofacker I L. The Vienna RNA Websuite. Nucleic Acids Res. 2008). (A) Folded structure. (B) Magnified view of the region of the mRNA containing the two CsrA binding sites. The "AGGA" motif in the loop of the stem-loop secondary structure for both binding sites recognized by CsrA is outlined with thick black lines. The secondary structure is crucial, as it can clearly be seen that the two binding sites are adjacent. Thus, modifications that affect the secondary structure in a way that would prevent the proximity of these two sites could have deleterious effects on CsrA binding potentially equal to modifications to the binding sites or "AGGA" recognition sequences themselves.

Figure 6:
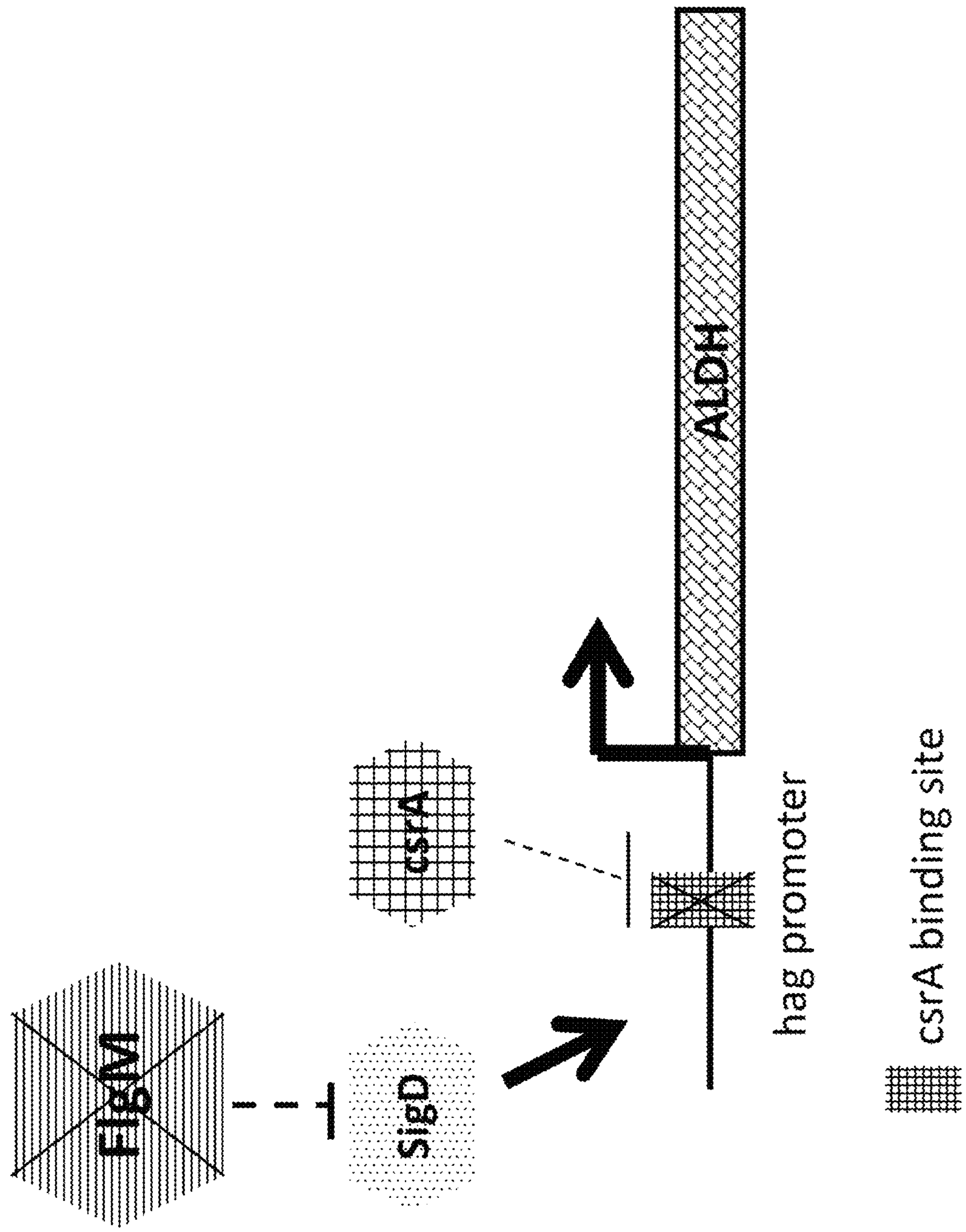

FIG. 6 shows a strategy for de-repression of expression from the hag promoter. Knock-out ("X") of the FlgM gene prevents FlgM inhibition of SigD activity. SigD activates (bold arrow) transcription of the hag promoter and operatively linked ALDH gene. Mutation ("X") of the csrA binding site on the hag promoter reduces inhibition of ribosome binding and translation of the ALDH gene. This results in robust expression (bold arrow) of ALDH protein.

SUMMARY

In one aspect disclosed herein is a recombinant microorganism comprising: a) a polynucleotide comprising an expression construct comprising a flagellin gene promoter operatively linked with a heterologous nucleotide sequence encoding a subject polypeptide, wherein the flagellin gene promoter comprises one or more genetic modifications that reduce CsrA repression of translation of an mRNA transcribed from the flagellin gene promoter; and b) a genetic modification of a flgM gene that reduces inhibition of SigD initiation of transcription. In one embodiment, the recombinant microorganism constitutively expresses the polypeptide. In another embodiment, the microorganism is probiotic. In another embodiment, the microorganism belongs to genus selected from *Bacillus, Bifidobacterium, Enterococcus, Escherichia, Lactobacillus, Leuconostoc, Pediococcus, Pediococcus* and *Streptococcus*. In another embodiment, the microorganism belongs to genus *Bacillus*. In another embodiment, the microorganism is *Bacillus subtilis* (*B. subtilis*). In another embodiment, the flagellin gene promoter is a hag promoter. In another embodiment, the hag promoter comprises one or more genetic modifications that reduce CsrA repression of translation of an mRNA transcribed from the flagellin gene promoter, wherein the genetic modification comprises modification of the CsrA BS1 binding site and/or CsrA BS2 binding site (e.g., nucleotide substitution, insertion or deletion). In another embodiment, the one or more genetic modifications comprise one or a plurality (e.g., two, three or four) of genetic modifications to the CsrA BS1 recognition sequence, AGGA, e.g., to the sequence AGAA. In another embodiment, the one or more genetic modifications comprise one or more genetic modifications in the 12-base-pair BS1 binding site or in the surrounding bases on either side of the binding site that form the stem of the stem-loop secondary structure of BS1. In another embodiment, the one or more genetic modifications comprise one or a plurality (e.g., at least 2, at least 3, at least 4, at least 5, at least 6, at least 7, at least 8, at least 9, at least 10, at least 11, at least 12) of genetic modifications in the BS1 binding site, gcacaaggacgt (SEQ ID NO: 8). In another embodiment, the one or more genetic modifications disrupt the stem and loop structure of BS1 by eliminating complementarity that allows hydrogen bonding. In another embodiment, the one or more genetic modifications comprise one or a plurality of genetic modifications in the sequence taagggcacaaggacgtgcctta (SEQ ID NO: 1) that are involved in hydrogen bonding, for example, to eliminate one, two, three, four or more hydrogen bond pairs. In another embodiment, the modified BS1 has the nucleotide sequence GCACAAGAACGT (SEQ ID NO: 2). In another embodiment, the one or more genetic modifications comprise one or more point mutations to the CsrA BS2 binding site. In another embodiment, the one or more genetic modifications comprise one or a plurality (e.g., at least 2, at least 3, at least 4, at least 5, at least 6, at least 7, at least 8, at least 9, at least 10, at least 11, at least 12, at least 13) of genetic modification in the 13-base-pair BS2 binding site or in the surrounding bases on either side of the binding site that form the stem of the stem-loop secondary structure of BS2 ATTCAGGGAGGAA (SEQ ID NO: 9). In another embodiment, the one or more genetic modifications disrupt the stem and loop structure of BS2 by eliminating complementarity that allows hydrogen bonding. In another embodiment, the modified BS2 has the nucleotide sequence ATTTAGGGAGGAA (SEQ ID NO: 3). In another embodiment, the one or more genetic modifications to the BS2 binding site does not include an alteration of nucleotides in the Shine-Dalgarno sequence agggagga. In another embodiment, wherein the flagellin gene promoter is located in a bacterial chromosome or in a plasmid. In another embodiment, the subject polypeptide is an aldehyde dehydrogenase. In another embodiment, the aldehyde dehydrogenase is AcoD from *Cupriavidus necator* and comprises an amino acid sequence identical to or substantially identical to: MNMAEIAQLGVSNPYKQQYENYIGGAWVPPAGGEYFESTTPITGKPFTRVPRSGQQDVDAAL DAAHAAKAAWARTSTTERANILNRIADRIEANLKLLAVAESIDNGKPVRETTAADLPLAVDHFRY FAGCIRAQEGGISEIDADTIAYHFHEPLGVVGQIIPWNFPLLMATWKLAPALAAGNCVVLKPAEQ TPASILVLMEVIGDLLPPGVVNVINGFGLEAGKPLASSPRISKVAFTGETTTGRLIMQYASQNLIP VTLELGGKSPNIFFEDVLAADDAFFDKALEGFAMFALNQGEVCTCPSRALIQESIYDRFMERAL KRVAAIRQGHPLDTGTMIGAQASAEQLEKILSYIDLGRKEGAQCLTGGERNVLDGDLAGGYYVK PTVFAGHNKMRIFQEEIFGPVVSVTTFKDEEEALAIANDTLYGLGAGVWTRDGARAFRMGRGI QAGRVWTNCYHAYPAHAAFGGYKQSGIGRENHRMMLDHYQQTKNLLVSYSPNALGFF [SEQ ID NO: 4]. In another embodiment, the aldehyde dehydrogenase is a human aldehyde dehydrogenase, e.g., having an amino acid sequence identical to or substantially identical to: MLRAAARFGPRLGRRLLSAAATQAVPAPNQQPEVFCNQIFINNEWHDAVSRKTFPTVNPS TGEVICQVAEGDKEDVDKAVKAARAAFQLGSPWRRMDASHRGRLLNRLADLIERDRTYLA ALETLDNGKPYVISYLVDLDMVLKCLRYYAGWADKYHGKTIPIDGDFFSYTRHEPVGVCG QIIPWNFPLLMQAWKLGPALATGNVWMKVAEQTPLTALYVANLIKEAGFPPGVVNIVPG FGPTAGAAIASHEDVDKVAFTGSTEIGRVIQVAAGSSNLKRVTLELGGKSPNIISDADM DWAVEQAHFALFFNQGQCCCAGSRTFVQEDIYDEFVERSVARAKSRVVGNPFDSKTEQGP QVDETQFKKILGYINTGKQEGAKLLCGGGIAADRGYFIQPTVFGDVQD GMTIAKEEIFGP VMQILKFKTIEEVVGRANNSTYGLAAAVFTKDLDKANYLSQALQAGTVWVNCYDVFGAQS PFGGYKMSGSGRELGEYGLQAYTEVKTVTVKVPQKNS [SEQ ID NO: 5]. In another embodiment, the genetic modification in a flgM gene comprises deletion of all or part of the flgM gene. In another embodiment, the genetic modification in a flgM gene comprises a single mutation or series of mutations in the sequence encoding active sites of flgM. In another embodiment, the genetic modification in a flgM gene disrupts secondary or tertiary structure, such as in one of the helices that defines FlgM secondary structure. In another embodiment, the genetic modification in a flgM gene comprises altering an amino acid in the 3rd or 4th helix at the C-terminal end of the FlgM protein, e.g., selected from I-58, K-62, I-65, G-68, D-73, A-78 of the *B. subtilis* FlgM. In another embodiment, the genetic modification in a flgM gene comprises altering one or more amino acids predicted to participate in FlgM binding to SigD, e.g., selected from I-3, G-7, S-10, V-11, A-40, K-41, M43, I-58, L-61, K-62, I-65, Y-70, K-71, V-72, D-73, A-74, H-76, I-77, A-78, N-80, M-81, I-82, N-83, F-84, Y-85, and K-86 of the *B. subtilis* FlgM.

In another aspect disclosed herein is a recombinant probiotic microorganism that constitutively expresses an aldehyde dehydrogenase. In one embodiment, the microorganism comprises: a) a polynucleotide comprising an expression construct comprising a flagellin gene promoter operatively linked with a heterologous nucleotide sequence encoding a subject polypeptide; and b) a genetic modification in a FlgM gene that reduces inhibition of SigD expression. In another embodiment, the flagellin gene promoter comprises one or more genetic modifications that reduce CsrA repression of translation of an mRNA transcribed from the promoter.

In another aspect disclosed herein is a polynucleotide comprising an expression construct comprising a flagellin gene promoter operatively linked with a heterologous nucleotide sequence encoding a subject polypeptide, wherein the flagellin gene promoter comprises one or more genetic modifications that reduce CsrA repression of translation of an mRNA transcribed from the flagellin gene promoter.

In another aspect disclosed herein is a method of making a polypeptide comprising culturing a recombinant microorganism as disclosed herein. In one embodiment, the method further comprises isolating the polypeptide.

In another aspect disclosed herein is a composition comprising a physiologically acceptable carrier and a recombinant probiotic microorganism, wherein the recombinant probiotic microorganism comprises: a) a polynucleotide comprising an expression construct comprising a flagellin gene promoter operatively linked with a heterologous nucleotide sequence encoding a subject polypeptide; and b) a genetic modification of a FlgM gene that reduces inhibition of SigD initiation of transcription. In one embodiment, the flagellin gene promoter comprises one or more genetic modifications that reduce CsrA repression of translation of an mRNA transcribed from the flagellin gene promoter. In another embodiment, the subject polypeptide is an aldehyde dehydrogenase. In another embodiment, the physiologically acceptable carrier is selected from lactic acid fermented foods, fermented dairy products, resistant starch, dietary fibers, carbohydrates, proteins and glycosylated proteins, water, capsule filler, and a gummy material.

In another aspect disclosed herein is a unit dose of a composition as disclosed herein, comprising about $10^4$ to about $10^{12}$ colony forming units of the recombinant probiotic microorganisms.

In another aspect disclosed herein is a method for preventing or treating an alcohol hangover, comprising administering to a subject in need thereof an effective amount of a composition comprising microorganisms that constitutively expresses aldehyde dehydrogenase. In another embodiment, the composition is administered before during or after the subject has consumed alcohol.

In another aspect disclosed herein is a method of metabolizing an analyte in a gut or in circulation in a subject comprising administering to the subject an effective amount of a composition comprising microorganisms that constitutively express an enzyme that metabolizes the analyte.

In another aspect disclosed herein is a method of producing a target compound comprising: a) contacting a culture comprising a recombinant microorganism expressing a subject polypeptide as disclosed herein with an analyte, wherein the subject polypeptide is an enzyme for which the analyte is a substrate, and b) culturing the microorganism, wherein the enzyme catalyzes the conversion of the analyte into the target compound. In one embodiment, the enzyme is selected from an amylase, a lipase and a protease.

DETAILED DESCRIPTION

I. Introduction

Disclosed herein is a microorganism, e.g., a bacterium, that has been genetically engineered to constitutively express an acetaldehyde dehydrogenase enzyme. The acetaldehyde dehydrogenase (ALDH) is expressed internally in the bacterial cell and gains access to its substrate, acetaldehyde, not by secretion of the enzyme, but by diffusion of the acetaldehyde into the bacteria. Acetaldehyde is a highly soluble molecule and can passively diffuse across cellular membranes. This internal location of the enzyme provides a functional advantage over secretion, as the interior of the bacterial cell is protected from the harsh and variable environment in the lumen of the gut, characterized by: low pH, hostile bacteria and eukaryotic cells that are looking to degrade free floating proteins for defense or nutritional purposes, high competition for enzymatic co-factors such as NAD, and extracellular proteases.

The flagellar regulatory machinery of *B. subtilis* was adapted to accomplish constitutive and robust expression of the ALDH. *B. subtilis* regulates motility by a sophisticated system involving several positive and negative regulators [2]. The basic strategy of this system is to remove negative regulators of the highly expressed flagellin gene, called hag.

The gene encoding the flagellar subunit of the *B. subtilis* flagellin is hag, and thus it is produced in hundreds of thousands of copies in a single bacterium in the right conditions, using a transcriptional promoter and a ribosome binding site that are both robust [3, 4].

Transcription is mediated by a sigma factor, SigD, which is repressed by the FlgM protein [5]. Deletion of flgM greatly enhances constitutive expression and activity of SigD, and consequently results in higher and more constitutive transcription of the flagellar operon and specifically the hag gene.

Translation of the hag gene is enabled by a highly robust ribosome binding site that is bound and repressed post-transcriptionally by a protein called CsrA [6]. However, a single point mutation in the CsrA binding site abrogates its binding and results in constitutive translation of the Hag protein [7].

Using the combination of deleting the flgM gene and making the single point mutation in the CsrA-binding site, one can achieve extremely high levels of Hag protein constitutively during the *B. subtilis* life cycle. Similarly, if the hag gene is replaced with a heterologous gene encoding a protein of interest, that gene can be transcribed and translated constitutively at high levels. Thus, by replacing the hag gene with a gene encoding an ALDH, and then deleting the flgM gene and making a single point mutation at the CsrA binding site of the hag promoter, robust and constitutive expression of our ALDH in *B. subtilis* was achieved.

Accordingly, in certain embodiments provided herein are microorganisms comprising a point mutation in the binding site of CsrA combined with a flgM deletion. By making these two mutations, the utility of any SigD-based or flagellin promoter systems is vastly increased by removing repression and making expression constitutive. Without wishing to be limited by theory, it is believed that this is distinct from a simple deletion of CsrA because CsrA is a pluripotent regulator in many bacterial species [8], and its deletion could have many other potentially undesirable phenotypic effects on the cell. By making a point mutation only in the binding site, the mutation precludes CsrA repression of the hag promoter specifically and uniquely, rather than removing CsrA repression from any other targets it may have.

This strategy is useful for constitutive expression of any desired polypeptide. This includes other enzymes that metabolize target analytes in the gut of an individual, or in the production of target molecules in industrial processes.

II. Definitions

As used herein, the term "probiotic microorganism" or "probiotic bacterium" refers to a microorganism or bacterium, which, when administered in an effective amount, confers a health or wellness benefit on a host.

As used herein, the term "recombinant microorganism" or "recombinant bacterium" refers to a microorganism or bacterium that comprises a polynucleotide comprising attached nucleotide sequences not normally attached to each other in nature.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotides or 4 consecutive amino acid residues that is compared to a reference sequence. The comparison window frequently has a length of at least 15 or at least 25 nucleotides or at least 5 or at least 8 amino acids. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, WI) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity.

Unless otherwise specified, the comparison window used to compare two sequences is the length of the shorter sequence.

Methods are described further in Natl. Acad. Sci. USA 85:2444; Higgins & Sharp (1988) Gene 73:237-244; Higgins & Sharp, CABIOS 5:151-153 (1989); Corpet et al. (1988) Nucleic Acids Research 16:10881-90; Huang et al. (1992) Computer Applications in the Biosciences 8:155-65; and Pearson et al. (1994) Methods in Molecular Biology 24:307-31. Alignment is also often performed by inspection and manual alignment.

A subject nucleotide sequence or amino acid sequence is "substantially identical" to a reference sequence if the subject amino acid sequence or nucleotide sequence has at least 70% sequence identity over a comparison window. Thus, sequences that have at least 80% sequence identity, at least 85% sequence identity, at least 90% sequence identity, at least 95% sequence identity, at least 98% sequence identity or at least 99% sequence identity with the reference sequence are also "substantially identical". Two sequences that are identical to each other are, of course, also "substantially identical".

In certain embodiments, the subject polynucleotide specifically hybridizes to a reference polynucleotide. "Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e. g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

As used herein, the term "transcription regulatory sequence" refers to a first nucleotide sequence that regulates transcription of a second nucleotide sequence to which it is operatively linked.

A "promoter" is a transcription regulatory sequence at least sufficient to promote the transcription of a nucleotide sequence in DNA into an RNA transcript. A transcript transcribed from a promoter typically includes sequences from the promoter downstream of the transcription start site, as well as downstream sequences that, in the case of mRNA, encode an amino acid sequence. Promoters are the best-characterized transcriptional regulatory sequences because of their predictable location immediately upstream of transcription start sites. Promoters include sequences that modulate the recognition, binding and transcription initiation activity of the RNA polymerase. These sequences can be cis acting or can be responsive to trans acting factors. Promoters, depending upon the nature of the regulation, can be constitutive or regulated. They are often described as having two separate segments: core and extended promoter regions.

The core promoter includes sequences that are sufficient for RNA polymerase recognition, binding and transcription initiation. The core promoter includes the transcriptional start site, an RNA polymerase binding site, and other general transcription binding sites and is where the pre-initiation complex forms and the general transcription machinery assembles. The pre-initiation complex is generally within 50 nucleotides (nt) of the transcription start site (TSS).

The core promoter also includes a sequence for a ribosome binding site, necessary for translation of an mRNA into a polypeptide.

The extended promoter region includes the so-called proximal promoter, which extends to about 250 nucleotides upstream of the transcriptional start site (i.e., −250 nt). It includes primary regulatory elements such as specific transcription factor binding sites. It has been found that many genes have transcription regulatory elements located further up-stream. In particular, a fragment that includes most of the transcription regulatory elements of a gene can extend up to 700 nt or more up-stream of the transcription start site. (See, e.g., U.S. 2007-0161031.) In certain genes, transcription regulatory sequences have been found thousands of nucleotides upstream of the transcriptional start site.

As used herein, a nucleotide sequence is "operatively linked" with a transcription regulatory sequence when the transcription regulatory sequence functions in a cell to regulate transcription of the nucleotide sequence. This includes promoting transcription of the nucleotide sequence through an interaction between a polymerase and a promoter.

As used herein, a first nucleotide sequence is "heterologous" to a second nucleotide sequence if the first nucleotide sequence is not operatively linked with the second nucleotide sequence in nature. By extension, a polypeptide is "heterologous" to an expression control sequence if it is encoded by nucleotide sequence heterologous the promoter.

As used herein, the term "homolog" refers to any naturally occurring gene from another genus or species than the one defined, or a distinct gene in the same strain or species that encodes for a protein having nearly identical folding and function. Studies have shown that between microorganisms, proteins with at least 30% amino acid identity to the gene or protein discussed have such properties (citation: PMID 23352839). Furthermore, the term "homolog" extends to genes that encode proteins with less than 30% identity to the gene or protein discussed but have been identified in a peer-reviewed scientific journal as a homolog of said gene or protein.

As used herein, the term "ortholog" refers to any homolog that occurs in another genus or species from the one discussed.

As used herein, the term "paralog" refers to any homolog that occurs in the same strain or species as the one discussed, often the result of gene duplication.

As used herein, the term "allelic variant" refers to a naturally occurring variation of a gene.

As used herein, the term "artificial variant" refers to a gene or protein comprising one or more genetic modifications to a naturally occurring gene or protein while retaining natural function.

As used herein, the term "mutation" refers to an alteration in a nucleotide sequence or amino acid sequence. A mutation can include a substitution of one or more nucleotides (a single nucleotide substitution is referred to as an "SNV" or "point mutation"), one or more nucleotide additions or one or more nucleotide deletions, as well as the changes in amino acid sequence, if any, resulting from these nucleotide alterations.

As used herein, a "derivative" of a bacterial strain is any genetically distinct version of that strain.

As used herein, the term "subject", when used in reference to an individual, refers to an individual animal, e.g., a human.

As used herein, the terms "therapy," "treatment," "therapeutic intervention" and "amelioration" refer to any activity resulting in a reduction in the severity of symptoms. The terms "treat" and "prevent" are not intended to be absolute terms. Treatment and prevention can refer to any delay in onset, amelioration of symptoms, mitigation of severity of symptoms, improvement in patient survival, increase in survival time or rate, etc. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects, the severity of the condition is reduced by at least 25%, 50%, 75%, 80%, or 90%, or in some cases, no longer detectable using standard diagnostic techniques.

As used herein, the term "probiotic composition" refers to a composition comprising probiotic microorganisms and a physiologically acceptable carrier. Typically, a probiotic composition confers a health or wellness benefit on the host subject to whom it is administered.

As used herein, the term "physiologically acceptable" refers to a carrier that is compatible with the other ingredients of a composition and can be safely administered to a subject. Probiotic compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The probiotic composition may be a liquid formulation or a solid formulation. When the probiotic composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the probiotic composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

As used herein, the probiotic composition could be formulated as a food composition, a dietary supplement, a functional food, a medical food or a nutritional product as long as the required effect is achieved, e.g. treatment or prevention of an alcohol hangover. Said food composition may be chosen from the group consisting of beverages, yogurts, juices, ice creams, breads, biscuits, crackers, cereals, health bars, spreads, gummies and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins.

The terms "effective amount" and "effective dose" refer to that amount of an agent effective to ameliorate a disorder or condition. For example, for the given parameter, an effective amount will show an increase or decrease of therapeutic effect at least any of 5%, 10%, 15%, 20%, 25%, 40%, 50%, 60%, 75%, 80%, 90%, or at least 100%. Efficacy can also be expressed as "-fold" increase or decrease. For example, an effective amount can have at least any of a 1.2-fold, 1.5-fold, 2-fold, 5-fold, or more effect over a control.

An effective amount of the agent is determined based on the intended goal. The term "unit dose" refers to a physically discrete unit suitable for use in a subject, each unit containing a predetermined quantity of the composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the composition also depend on the judgment of the practitioner and are peculiar to each individual.

The terms "dose" and "dosage" are used interchangeably herein. A dose refers to the amount of active ingredient given to an individual at each administration. For the present invention, the dose can refer to the number of bacteria, e.g., the amount of colony forming units (CFU). The dose will vary depending on a number of factors, including frequency of administration; size and tolerance of the individual; severity of the condition; risk of side effects; the route of administration. One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a beverage for oral consumption.

III. Expression Constructs

Contemplated here are methods that reduce either or both of inhibition of transcription from the flagellin promoter and inhibition of translation of an mRNA transcript from a flagellin promoter.

Certain polynucleotides disclosed herein comprise an expression construct comprising a flagellin gene transcription regulatory sequence, e.g., a promoter, operatively linked with a heterologous nucleotide sequence encoding a subject polypeptide, that is, a polypeptide subject to expression. In certain embodiments, the hag promoter comprises genetic alterations such that, upon transcription of an mRNA from the hag promoter, CsrA inhibition of mRNA translation is repressed.

A. Flagellin Gene Transcription Regulatory Sequences

Many bacteria have a flagellin gene homolog. The gene goes by many names, some examples of which are: hag in *B. subtilis*; fliC in *Escherichia coli, Bacillus thuringiensis*, and several *lactobacillus* species; and flaA or flaB/C/D/E/F/etc. in *Legionella* species, *Vibrio* species, and *Campylobacter* species.

In one embodiment, the flagellin gene promoter is a hag gene promoter. The flagellin homolog is hag in *Bacillus*, e.g., *B. subtilis*. In another embodiment, the flagellin gene promoter is native to the microorganism in which the subject protein is to be expressed. For example, this can be the case when the expression construct is located in a bacterial chromosome.

As used herein, the term "Hag" (or "hag" or "hag") refers to the protein (or gene encoding such protein) annotated as "Hag" in *B. subtilis* or any homolog in the same or other genus, species, or strain, which is the structural subunit also known more generically as "flagellin" used to assemble a flagellum. It is known by several other names in other genera, species, and strains. It is defined in *B. subtilis* by the sequence:

[SEQ ID NO: 6]

atgagaattaaccacaatattgcagcgcttaacacactgaaccgtttgtc ttcaaacaacagtgcgagccaaaagaacatggagaaactttcttcaggtc ttcgcatcaaccgtgcgggagatgacgcagcaggtcttgcgatctctgaa aaaatgagaggacaaatcagaggtcttgaaatggcttctaaaaactctca agacggaatctctcttatccaaacagctgagggtgcattaactgaaactc atgcgatccttcaacgtgttcgtgagctagttgttcaagctggaaacact ggaactcaggacaaagcaactgatttgcaatctattcaagatgaaatttc agctttaacagatgaaatcgatggtatttcaaatcgtacagaattcaatg gtaagaaattgctcgatggcacttacaaagttgacacagctactcctgca aatcaaaagaacttggtattccaaatcggagcaaatgctacacagcaaat ctctgtaaatattgaggatatgggtgctgacgctcttggaattaaagaag ctgatggttcaattgcagctcttcattcagttaatgatcttgacgtaaca aaattcgcagataatgcagcagatactgctgatatcggtttcgatgctca attgaaagttgttgatgaagcgatcaaccaagtttcttctcaacgtgcta agcttggtgcggtacaaaatcgtctagagcacacaattaacaacttaagc gcttctggtgaaaacttgacagctgctgagtctcgtatccgtgacgttga catggctaaagagatgagcgaattcacaaagaacaacattctttctcagg cttctcaagctatgcttgctcaagcaaaccaacagccgcaaaacgtactt caattattacgttaa.

As used herein, the term "hag promoter" refers to a naturally occurring flagellin gene promoter cognate from genus *Bacillus* and promoters having sequences substantially identical thereto or hybridizing specifically thereto. In *B. subtilis*, the hag promoter is comprised in a 273 base-pair sequence 5' of the start codon of the hag gene. It has the nucleotide sequence:

[SEQ ID NO: 7]

ggaattgacgccccaaagcatattgatattcacaggaaagaaatttactt gaccattcaggaagaaaataaccgtgcagcagcgttatccagcgatgtga tctccgcattatcctcacaaaaaaagtgaggatttttttatttttgtatt aacaaaatcagagacaatccgatattaatgatgtagccgggaggaggcgc

-continued aaaagactcagccagttacaaaataagggcacaaggacgtgccttaacaa catattcagggaggaacaaaacaATG (where "ATG" represents the start codon of hag). It is expected that the sequence in bold beginning with TTAA (underlined) through the start codon ATG suffices to promote gene expression.

In particular, the hag promoter contains a SigD recognition sequence defined by a "ttaa" sequence (underlined), which is the −35 SigD RNA polymerase binding site and a "tccgatat" sequence (underlined), which is the −10 SigD RNA polymerase binding site. In addition, hag has two CsrA binding sites defined by the sequences "gcacaaggacgt" [SEQ ID NO: 8] (high-affinity binding site 1, or "BS1") (underlined) and "attcagggaggaa" [SEQ ID NO: 9] (low-affinity binding site 2, or "B52") (underlined). The hag promoter is also defined by a Shine-Dalgarno sequence "agggagga". The overall structure of the hag promoter is illustrated in FIG. 4.

As used herein, the term "CsrA" ("Carbon storage regulator A") refers to the protein (or gene encoding such protein) annotated as "CsrA" in *B. subtilis*—or any homolog or ortholog in another genus or species, or paralog in the same species. CsrA is homologously referred to as RsmA in some species. CsrA protein binds to a stem-loop RNA motif having the consensus sequence AGGA in the loop, thereby inhibiting translation into polypeptide of a nucleotide sequence incorporated in an mRNA comprising the consensus sequence. CsrA can inhibit expression of an mRNA transcribed from the hag promoter either directly by binding to the RNA and preventing translation or indirectly by binding to another RNA that encodes a protein that otherwise regulates flagellar expression. CsrA is defined in *B. subtilis* by the sequence:

[SEQ ID NO: 10]

atgctagttttatcgcggaaaataaacgaagcgattcaaataggtgctg atattgaagtaaaagtgattgcggttgaaggggatcaagtgaagcttgg aattgacgccccaaagcatattgatattcacaggaaagaaatttacttg accattcaggaagaaaataaccgtgcagcagcgttatccagcgatgtga tctccgcattatcctcacaaaaaaagtga.

In certain embodiments, expression constructs of this disclosure comprise genetic modifications in a flagellin gene promoter that, upon transcription from the promoter into a transcript, such as mRNA, repress CsrA inhibition of mRNA translation. This disclosure contemplates several genetic modifications to a flagellin gene promoter, and, in particular, to the hag promoter, to achieve this result. In some embodiments, genetic modifications to hag to inhibit CsrA repression of translation can comprise an alteration of a stem and loop structure in either or both of BS1 or BS2. In some embodiments, the genetic modification is an insertion or a deletion of one or more nucleotides.

The genetic modification can be one or more point mutations to binding to the CsrA BS1 binding site. BS1 can be modified by altering one or a plurality (e.g., two, three or four) nucleotides in the CsrA recognition sequence, AGGA. For example, the AGGA binding motif of BS1 can be modified to AGAA. Alternatively, the genetic modification can comprise one or more mutations in the 12-base-pair BS1 binding site or in the surrounding bases on either side of the binding site that form the stem of the stem-loop secondary structure of BS1. This includes, for example, modification of one or a plurality (e.g., at least 2, at least 3, at least 4, at least 5, at least 6, at least 7, at least 8, at least 9, at least 10, at least 11, at least 12) of nucleotides in the BS1 binding site, gcacaaggacgt (SEQ ID NO: 8). Alternatively, a genetic alteration can disrupt the stem and loop structure of BS1 by eliminating complementarity that allows hydrogen bonding. Such alterations can be made as one or a plurality of mutations in the sequence

[SEQ ID NO: 1]

taaggg<u>cacaaggacgt</u>gcctta involved in hydrogen bonding, for example, to eliminate one, two, three, four or more hydrogen bond pairs. In one embodiment, the modified BS1 has the nucleotide sequence GCACAAGAACGT [SEQ ID NO: 2].

The genetic modification can be one or more point mutations to binding to the CsrA BS2 binding site. This includes one or a plurality (e.g., at least 2, at least 3, at least 4, at least 5, at least 6, at least 7, at least 8, at least 9, at least 10, at least 11, at least 12, at least 13) of mutations in the 13-base-pair BS2 binding site or in the surrounding bases on either side of the binding site that form the stem of the stem-loop secondary structure of BS2. This also includes a genetic alteration that disrupts the stem and loop structure of BS2 by eliminating complementarity that allows hydrogen bonding. For example, the modified BS2 can have the nucleotide sequence ATTTAGGGAGGAA [SEQ ID NO: 3]. In certain embodiments, the modification does not include an alteration of nucleotides in the Shine-Dalgarno sequence agggagga.

It will be recognized that the genetic modification, while inhibiting CsrA binding, is selected to allow the mRNA to retain ribosome binding activity and to permit translation.

The heterologous nucleotide sequence is heterologous to the flagellin promoter. That is, it is a sequence not normally under the control of the hag promoter in nature and, typically, encodes a polypeptide whose expression is not under the control of the flagellin promoter. The subject polypeptide can be any polypeptide desired to be expressed. In certain embodiments, the polypeptide is an aldehyde dehydrogenase.

B. Subject Polypeptide

The heterologous nucleotide sequence can be placed under operative linkage with the flagellin promoter by any method known in the art. For example, the heterologous nucleotide sequence can be integrated into the bacterial chromosome. Alternatively, the heterologous nucleotide sequence can be attached to a flagellin promoter in a plasmid that is introduced into the microorganism. A heterologous nucleotide sequence can be targeted to the hag promoter by, for example, homologous recombination, as described, for example, in PMID: 4994568. Another useful method involves transposon technology. Transposons can target specific sequences in a chromosome and insert and attached a nucleotide sequence there. Materials for transposon integration are available from, e.g., Lucigen (Middleton, WI), which commercializes the EZ-Tn5 Transposase.

The polypeptide to be the subject of expression ("subject polypeptide") can be any polypeptide desired. Such polypeptides can be those desired to be expressed constitutively for the purpose of obtaining high amounts of the polypeptide. The polypeptide can be a biologic drug, a food protein, such as albumin, or an enzyme in a biochemical pathway, such as alpha-galactosidase A. In certain embodiments, the polypeptide is an enzyme that metabolizes analytes likely to be found in the gut of an animal. Such analytes can be found there through ingestion, through production by the microbiome, through production by the subject, or through diffusion or active transport across the membranes of the gut. Such polypeptides include for example: peptidases like dipeptidyl peptidase IV; and lipases like human pancreatic lipase.

In one embodiment, the polypeptide is an aldehyde dehydrogenase. As used herein, the term "aldehyde dehydrogenase" or "ALDH" refers to any enzyme that is known or predicted to use acetaldehyde as a substrate and catalyze it into a distinct product. Most commonly this is an enzyme whose function is known or predicted to catalyze the oxidation of aldehydes. Generally, this refers to enzymes of the classification EC 1.2.1.-, which catalyze the oxidation of an aldehyde to a carboxylic acid using NAD(P) as a co-factor. It includes enzymes which oxidize acetaldehyde to acetate/acetic acid (e.g. EC 1.2.1.3, 1.2.1.4, and 1.2.1.5), and acetylating enzymes which convert coenzyme A to acetyl-coenzyme A (e.g. EC 1.2.1.10). It also refers to enzymes which use other defined acceptors, including (but not limited to): enzymes using a quinone (e.g. of the classification EC 1.2.5.-), or other unknown acceptors (e.g. of the classification EC 1.2.99.-).

In certain embodiments, the aldehyde dehydrogenase is a human aldehyde dehydrogenase (e.g., ALDH2) or a non-human aldehyde dehydrogenase (e.g., AcoD or AldB). The aldehyde dehydrogenase can be a bacterial aldehyde dehydrogenase and the microorganism in which is it is expressed is a bacterium. The aldehyde dehydrogenase can be native to the microorganism in which the gene is to be expressed.

The subject polypeptide is expressed by placing a nucleotide sequence encoding the polypeptide under transcriptional regulatory control of the flagellin promoters described herein. Nucleotide sequences encoding many genes can be found in publicly available databases such as NCBI, uniprot, KEGG, BRENDA, etc. Polynucleotides encoding the amino acid sequences of these polypeptides can be linked to the promoter by methods well known in the art of molecular biology. In one embodiment, the subject polypeptide is not lacZ.

IV. Disruption of Repressor of Sigma Factors

Sigma factors, such as SigD and its homologs, initiate flagellin synthesis. FlgM and its homologs function as repressors of Sigma factor activity. This disclosure provides for de-repression of Sigma factor activity by disruption of Sigma factor repressors such as FlgM.

As used herein, the term "FlgM" refers to the protein (or the gene encoding such protein) annotated as "FlgM" in *B. subtilis*, or any homolog in another genus or species, which inhibits the sigma factor responsible for recruiting RNA polymerase to late flagellar genes for transcription. This inhibited sigma factor is called SigD in *B. subitlis*, FliA in *E. coli*, or potentially other names such as sigma 28 in other genera and species in which said sigma factor has a homolog. FlgM is defined in *B. subtilis* by the sequence:

[SEQ ID NO: 11]

atgaaaatcaatcaatttggaacacaatccgttaatccatatcaaaaaaat tatgataagcaagcggtgcaaaaaactgttgcacaacctcaagataaaatt gaaatttcatcacaggctaaagaaatgcaacatgcatccgacgcagtcact -continued

```
ggttcacgacaggaaaaaattgcgcagcttaaagcgcaaattgaaaacggg

tcatacaaagtagacgcaaatcatattgcgaaaaatatgattaatttttat

aaaaagcaataa.
```

As used herein, the term "SigD" refers to the sigma factor (or the gene encoding it) in *B. subtilis* responsible for, among other things, recruiting the RNA polymerase to late flagellar genes for transcription. "SigD" furthermore refers to homologs in other species, such as FliA in *E. coli*, or the broader denotation of sigma-28 in several species. SigD is defined in *B. subtilis* by the sequence:

```
                                            [SEQ ID NO: 12]
atgcaatccttgaattatgaagatcaggtgctttggacgcgctggaaaga

gtggaaagatcctaaagccggtgacgacttaatgcgccgttacatgccgc

ttgtcacatatcatgtaggcagaatttctgtcggactgccgaaatcagtg

cataaagacgatcttatgagccttggtatgcttggtttatatgatgccct

tgaaaaatttgaccccagccgggacttaaaatttgatacctacgcctcgt

ttagaattcgcggcgcaatcatagacgggcttcgtaaagaagattggctg

cccagaacctcgcgcgaaaaaacaaaaaaggttgaagcagcaattgaaaa

gcttgaacagcggtatcttcggaatgtatcgcccgcggaaattgcagagg

aactcggaatgacggtacaggatgtcgtgtcaacaatgaatgaaggtttt

tttgcaaatctgctgtcaattgatgaaaagctccatgatcaagatgacgg

ggaaaacattcaagtcatgatcagagatgacaaaaatgttccgcctgaag

aaaagattatgaaggatgaactgattgcacagcttgcggaaaaaattcac

gaactctctgaaaaagaacagctggttgtcagtttgttctacaaagagga

gttgacactgacagaaatcggacaagtattaaatctttctacgtcccgca

tatctcagatccattcaaaggcattatttaaattaaagaatctgctggaa

aaagtgatacaataa.
```

FlgM binds to SigD via several residues, the majority of which are located in the 4th helix at the C-terminal end of the FlgM protein. Targets for inactivation would be mutation of the highly conserved residues in the 3rd and 4th helices corresponding to 1-58, K-62, 1-65, G-68, D-73, A-78 of the *B. subtilis* FlgM. More broadly, any one or combination of the 26 residues directly involved in binding to SigD (as identified in PMID: 15068809) could be mutated to potentially generate a protein with reduced or null activity. Alternatively, any mutation or combination of mutations that disrupted the secondary or tertiary structure—in particular the 4 helices that define the secondary structure—could potentially successfully reduce or attenuate the ability of FlgM to inhibit SigD.

In some embodiments, the recombinant microorganism comprises a genetic modification that reduces the ability FlgM to inhibit SigD activity. In particular, one such genetic modification is partial or complete deletion of the FlgM gene to reduce or eliminate its biological activity. Partial deletion can include deletion of part of the gene encoding at least 25% of the C-terminus of the protein.

Other genetic modifications include, for example, frameshift mutations producing an inactive FlgM protein, or disruption of the FlgM promoter. Alternatively, FlgM could be rendered inactive by a point mutation that renders it functionally inactive or otherwise inhibits its ability to bind to or otherwise repress SigD. Indirectly, FlgM could be disrupted by making it insensitive to activators such as ComK or DegU, or by making it overly sensitive to repressors such as ScoC or proteases Epr and Wpr.

V. Recombinant Microorganisms

Recombinant microorganisms contemplated for use herein comprise an expression system including at least an expression construct comprising a flagellin gene promoter operatively linked with a heterologous nucleotide sequence encoding a subject polynucleotide for expression, which flagellin gene promoter is genetically modified to reduce CsrA inhibition of translation; and, optionally, a FlgM gene genetically modified to reduce suppression of SigD expression.

The recombinant microorganism is typically a probiotic microorganism that is safe for ingestion by an animal, e.g., a human. Probiotic microorganisms include, without limitation, from *Bacillus, Bifidobacterium, Enterococcus, Escherichia coli, Lactobacillus, Leuconostoc, Pediococcus* and *Streptococcus*. In particular, this disclosure contemplates the use of bacteria of genus *Bacillus* and more particularly, *B. subtilis*. Microorganisms can be obtained from any typical source including, for example, the American Type Culture Collection (ATCC) or the *Bacillus* Genetic Stock Center (BGSC).

In certain embodiments, the microorganism is not a eukaryote. For example, the microorganism is not a eukaryote used for fermentation of alcoholic beverages, such as *Saccharomyces.*

VI. Probiotic Compositions

Also provided herein are compositions comprising probiotic microorganisms. The compositions comprise recombinant microorganisms as provided herein in a physiologically acceptable carrier.

In certain embodiments, the probiotic compositions are provided in a unit dose. A unit dose will typically have between $10^4$ to $10^{12}$ colony forming units of the microorganism in a suitable carrier. This includes any effective dose as described herein. The total volume of the dose can be between about 0.05 mL and 500 mL, e.g., between about 0.5 mL and about 50 mL or between about 2.5 mL and 15 mL.

VII. Methods of Use

Also provided herein are methods of using recombinant microorganisms and probiotic compositions to metabolize target analytes and/or to provide health or wellness benefits on the host.

The host can be any animal. This includes, for example, mammals, e.g., primates, e.g., humans. Mammals can belong to any class, such as, artiodactyla, carnivora, cetacean, chiroptera, dermoptera, edentata, hyracoidae, hyracoidae, insectivore, lagomorpha, marsupialia, monotremata, perissodactyla, ungulate, pholidata and pinnipedia.

A host can ingest a probiotic composition of this disclosure in an amount effective to produce the intended result. The intended result can be metabolism of a target analyte in the gut of the host. In this case, the subject polypeptide can be an enzyme that processes the analyte. In particular, this disclosure contemplates metabolism of acetaldehyde, a product of ethanol metabolism, which is a cause of alcohol hangover.

As used herein, the term "alcohol hangover" refers to a condition resulting from consumption of alcohol and characterized by one or more of: dehydration, poor sleep, grogginess, nausea, vomiting, headache, malaise, dry mouth, sensitivity to light and sound, sweating, muscle pain, diarrhea, stomach pain, gastrointestinal distress, vertigo, anxiety, depression, irritability, and elevated acetaldehyde concentration in the body.

Prevention or treatment, e.g., mitigation, of alcohol hangover can involve administering a probiotic composition of this disclosure to a subject before, during or after consumption of alcohol. The composition can be ingested up to any of twenty-four hours, eighteen hours, twelve hours, eleven hours, ten hours, nine hours, eight hours, seven hours, six hours, five hours, four hours, three hours, two hours or one hour before alcohol consumption begins. The probiotic composition can be administered during alcohol consumption. The probiotic composition can be administered up to any of twelve hours, eleven hours, ten hours, nine hours, eight hours, seven hours, six hours, five hours, four hours, three hours, two hours or one hour after alcohol consumption or at any time a subject suffers from symptoms of alcohol hangover.

The composition can be administered to the gut (e.g., stomach or intestines) of the individual, either by oral consumption or through the anus. Living, rather than non-living microorganisms can be administered to the individual. The microorganisms can be provided in a different composition than the alcoholic beverage, that is, can be taken separately from the alcoholic beverage. This can be the case, for example, when the composition is administered before consumption of alcohol.

The effective dose of the probiotic can depend on the extent of symptoms of alcohol hangover. Generally, the dosage of recombinant bacteria will vary depending upon such factors as the subject's age, weight, height, sex, general medical condition and previous medical history. In specific embodiments, it may be desirable to administer the bacterium in the range of about $10^4$ to about $10^{12}$ CFU, $10^5$ to $10^{11}$ CFU, $10^6$ to $10^{10}$ CFU, $10^8$ to $10^{10}$ CFU or $10^8$ to $10^{12}$ CFU ("colony forming units") of the microorganism.

In another embodiment, microorganisms disclosed herein are used for the production of a desired composition. Methods to produce such compositions can involve culturing a recombinant microorganism that constitutively expresses an enzyme that transforms a target analyte into the desired composition or an intermediate in the production of the desired composition. In this case, the target analyte is added to the microorganism culture and incubated for a time sufficient to produce the enzymatic product.

EXAMPLES

Example 1

Methods:

Strains, Plasmids, and Media

The *B. subtilis* strain PY79 from the *Bacillus* Genetic Stock Center was used (strain 1A747) for all manipulations. All *B. subtilis* strains used here are derivatives of PY79.

Unless otherwise noted, bacteria were grown in LB medium (1% tryptone, 0.5% yeast extract, 0.5% sodium chloride, [1.5% agar if solid medium]). For MLS resistance selection, 1 ug/mL erythromycin and 25 ug/mL lincomycin were used. For transformation experiments, bacteria were grown in modified competence (MC) medium (100 mM phosphate buffer, 2% glucose, 3 mM trisodium citrate, 22 mg/L ferric ammonium citrate, 0.1% casein hydrolysate, 0.16% glutamic acid, 3 mM magnesium sulfate).

Plasmid used to make genetic modifications is pMiniMAD [9].

Plasmid used for IPTG-induced expression under pHyspank promoter is pDR111 [10]. 1 mM IPTG was used for all inductions.

flgM Deletion

An in vitro transcribed double-stranded DNA molecule containing ~800 base pairs 5' and 3' of the flgM gene from *B. subtilis* PY79, along with the first and last 15 base pairs of the coding sequence of flgM separated by a PstI restriction enzyme recognition sequence (see full sequence in table 1) was constructed. pMiniMAD was then linearized using primers ZP24 and ZP25 (table 1). The resulting PCR product and the delta flgM sequence were then ligated together to create pMiniMAD delta-flgM using Gibson assembly [11]. The resulting plasmid was transformed into *E. coli* via heat transformation. Plasmid was miniprepped using a commercially available kit, and that miniprepped plasmid was used as the DNA source to do the deletion as follows:

i. Single colony of PY79 inoculated in 2 mL of MC medium in 15 mL test tube
ii. Grow culture at 37° C. with shaking at 275 rmp for 4.5 hours, or −1 hour after exiting exponential growth
iii. Transfer 400 uL of culture to new 15 mL test tube and add lug of miniprepped plasmid (described above)
iv. Return culture with DNA to shaker at 37° C. for 1.5 hours
v. Plate culture on LB agar with 1 ug/mL erythromycin and 25 ug/mL lincomycin
vi. Incubate overnight at 37° C.
vii. Screen isolated colonies for mutant allele via PCR using primers ZP77 and ZP78, and inoculate positive colony in 3 mL LB broth without antibiotics
viii. Grow overnight at room temperature with shaking at 275 rpm
ix. Isolation streak 10 uL of overnight culture on LB without antibiotics and grow at 37° C. overnight. Because of the lack of antibiotic selection, plasmid can be lost during overnight replication. The observed stability of this plasmid is about 90%, with about 1 colony in 10 losing the plasmid at this stage.
x. Duplicate streak isolated colonies on LB with and without antibiotics (1 ug/mL erythromycin and 25 ug/mL lincomycin), and grow overnight at 37° C.
xi. PCR screen antibiotic sensitive colonies with primers ZP77 and ZP78 to identify strains with the mutant allele

TABLE 1

Primers and constructed genes/alleles

| Primer | Description | Sequence |
|---|---|---|
| ZP24 | Fwd pMiniMAD for gibson | CTGGCGTTACCCAACTTAATC [SEQ ID NO: 13] |

TABLE 1-continued

| Primers and constructed genes/alleles | | |
|---|---|---|
| Primer | Description | Sequence |
| ZP25 | Rev pMiniMAD for gibson | CTTGGCGTAATCATGGTCATAG [SEQ ID NO: 14] |
| ZP77 | flgM fwd | GAGGAAACAGGTGTGGAAGAAG [SEQ ID NO: 15] |
| ZP78 | flgM rev | GGTCATCTTCTGTCTGCGTG [SEQ ID NO: 16] |
| | delta flgM allele | CTATGACCATGATTACGCCAAGTGAATAATGAGAAACAGTCAAA<br>GAAAAAGAAAACAGAACGCCTGCTGTCAGAGTGCATTTTTGATA<br>CAAAAAATAATTCAGCAGAAGGTATGAATATCATTTTAATAGAC<br>GATCTTTATACAACAGGCGCCACCTTGCACTTCGCAGCCCGCT<br>GCTTATTAGAAAAAGGAAAAGCCGCTTCAGTGTCATCTTTTACC<br>TTGATCAGAAGCTAAATGATTCTGTTTTTATGCCGATATAATCAC<br>TAGAAATTGACACAGGCATATTATCTAATAAGGAGAAAAAAAGA<br>TGGGAGAACTGGCTAATTGTCCGAAATGCAATGCTTTATTTTTA<br>AAAACAAAGCTGCAAACCGTATGTCAGGCGTGTATTAAGGAAG<br>AAGAAAAATCATTTGAGACTGTCTATAAATTTTTAAGAAAACAGG<br>AAAACCGGCAATCAACTTTGAGCCGGATAACTGAGGAAACAGG<br>TGTGGAAGAAGAGCTGATATTGAAATTCATCAGGCAGAAGCGA<br>ATTCAGATCACTCATCTTCCTAATTTGGCATACCCTTGTGAAAG<br>GTGCGGGACATCGATTAGAGAAGGCAAGTTCTGCAAGGCTTGC<br>CAGTCTGATATTAAGGATCAAATGGATCATTTGAACCACGAGGA<br>TGCTCTGAAAATCGAGAAAGAAAATAGTAAAAAAGACACATACT<br>ATGCCTATAATACCAAAAACAGCTGATTCCCTAAACTAACTGAA<br>AACGCAGTCGATAAAAGGGTTAAGATTGTTTAAAGACTGCAACG<br>GAAAGCGAGAGGAATCCTATGAAAATCAATCAACTGCAGTTTTA<br>TAAAAAGCAATAAAAAAGGAGAAAGCCCATGTCAGCGAAGGCA<br>ATTATTGAACAATTGAAGCGACTTTGCGTTCTGCATGAGCACCT<br>GCTCACGCTGTCTGAAGAAAAGACGGAAGCGCTCAAAGCCGG<br>CAAAACAAAAGAGCTTTCTAACATTTTGACAAAAGAGCAAAAAT<br>ATATTCAAGCAATCACGCAGACAGAAGATGACCGGATCAAAAC<br>AACTTCGGCCTTTCTCGGATATAGCGAAAATAATACTATTTCCG<br>CATGTATCGCCAAAACCTCAGGCAGTGAAAAGGAAGAGCTGGA<br>ACAACTATACGAATCTCTTTCTCAAGTTCTCGGACGTCTGAAAA<br>AAGTAAATGAGATGAATAGGCAGCTGACAAGAGACGCGCTGCA<br>ATTCATCTCTATTTCGTACGATATGCTGGTTCCTAAGGAAAATAA<br>CTTCAATTACAGCAAATCAATTAAAGCTGAGCTGCCGAAAAGTA<br>GCAAAATGAAACTGTTTGATTCAAAAGCTTAGCAGAAAGGAATT<br>CAGAAAATGACATCTACCTTTATGGGGCTTGAAACTGCAAGGC<br>GGGCGTTAAGCGCTCAGCAGGCAGCGTTAAGCACTACTGCAAA<br>TAACGTGGCAAATGCCAATACTGATGGTTATACAAGACAGCGG<br>GTCTCATTGGAGGCAACTGACTATTTCCCTGCTGTATCTAAAAA<br>TGCAGAAAAAACAGCGGGACAAATGGGTACGGGCGTTCAAGG<br>AAAATCAGTTGAGAGAATAAGAGATATCTTTCTTGACTACCAAT<br>ACCGTCTTCAAAACCTGGCGTTACCCAACTTAATC [SEQ ID NO: 17] |
| | phag + GFP | CTATGACCATGATTACGCCAAGTGAACAATGATCATTCATACGA<br>AGTACCATGGCCAAATGAACATAAAAGAAGAACAAATCATTCTT<br>TTTGAAAGCGGGATTCCAGGCTTTTTAGAAGAAAAACAGTTCGT<br>CATACTTCCGCTTTCAGAAGACTCTCCATTCGTGGCACTGCAGT<br>CCGTCACTTCAGAAAATCTTGCGTTTATCGTCGTAAGTCCGTTT<br>ATCTTTTTTAAGAATTATGAATTTGATCTTGATGAATCAACTGCT<br>GAACTTTTGGATATCGATAATATTCAAGACGTAGAAGTCATGAC<br>AATATTGACTATGGCAGAGCCATTTGAAAAGTCTACTGCGAATT<br>TATTGGCTCCCATTATTGTGAATCGCAAGAACATGATGGCTAAG<br>CAAGTCGTTTTACACGACTCCTCATATACGACAAAGCATCCGAT<br>TGGAGGAGAATCATGCTAGTTTTATCGCGGAAAATAAACGAAG<br>CGATTCAAATAGGTGCTGATATTGAAGTAAAAGTGATTGCGGTT<br>GAAGGGGATCAAGTGAAGCTTGGAATTGACGCCCCAAAGCATA<br>TTGATATTCACAGGAAAGAAATTTACTTGACCATTCAGGAAGAA<br>AATAACCGTGCAGCAGCGTTATCCAGCGATGTGATCTCCGCAT<br>TATCCTCACAAAAAAAGTGAGGATTTTTTTATTTTTGTATTAACA<br>AAATCAGAGACAATCCGATATTAATGATGTAGCCGGGAGGAGG<br>CGCAAAAGACTCAGCCAGTTACAAAATAAGGGCACAAGAACGT<br>GCCTTAACAACATATTCAGGGAGGAACAAAACAATGCGTAAAG<br>GAGAAGAACTTTTCACTGGAGTTGTCCCAATTCTTGTTGAATTA<br>GATGGTGATGTTAATGGGCACAAATTTTCTGTCAGTGGAGAGG<br>GTGAAGGTGATGCAACATACGGAAAACTTACCCTTAAATTTATT<br>TGCACTACTGGAAAACTACCTGTTCCATGGCCAACACTTGTCAC<br>TACTTTCGGTTATGGTGTTCAATGCTTTGCGAGATACCCAGATC<br>ATATGAAACGGCATGACTTTTTCAAGAGTGCCATGCCCGAAGG<br>TTATGTACAGGAAAGAACTATATTTTTCAAAGATGACGGGAACT<br>ACAAGACACGTGCTGAAGTCAAGTTTGAAGGTGATACCCTTGTT<br>AATAGAATCGAGTTAAAAGGTATTGATTTTAAAGAAGATGGAAA |

TABLE 1-continued

Primers and constructed genes/alleles

| Primer | Description | Sequence |
|---|---|---|
| | | CATTCTTGGACACAAATTGGAATACAACTATAACTCACACAATG<br>TATACATCATGGCAGACAAACAAAAGAATGGAATCAAAGTTAAC<br>TTCAAAATTAGACACAACATTGAAGATGGAAGCGTTCAACTAGC<br>AGACCATTATCAACAAAATACTCCAATTGGCGATGGCCCTGTCC<br>TTTTACCAGACAACCATTACCTGTCCACACAATCTGCCCTTTCG<br>AAAGATCCCAACGAAAAGAGAGACCACATGGTCCTTCTTGAGT<br>TTGTAACAGCTGCTGGGATTACACATGGCATGGATGAACTATAC<br>AAATAATTTTAAAAAAGACCTTGGCGTTGCCAGGGTCTTTTAATT<br>TAAATTTCTATCTCCTAATCATTCCTCATCCTGTCACTAACTCAT<br>GATATAATAACCGGATTCTCCACTAACTTTTTATAAATGTATTTC<br>CATACAAGAAATCTAAAACAGAAGATTTTTTTCCAAAAATATGTG<br>TAATCTTATCTCGACTTAGTCGATATAAACGATAGATTGGGGCA<br>TAGGGGATGATCAATTGAACATTGAAAGGCTCACTACGTTACAA<br>CCTGTTTGGGATCGTTATGATACTCAAATACATAATCAGAAAGA<br>TAATGATAACGAGGTTCCTGTTCATCAAGTTTCATATACCAATCT<br>TGCTGAAATGGTGGGGGAAATGAACAAGCTTTTGGAACCTTCG<br>CAAGTTCATCTGAAGTTCGAGCTTCATGACAAGTTAAATGAATA<br>CTATGTAAAGGTAATAGAGGACTCTACAAATGAAGTGATCCGC<br>GAAATTCCACCAAAACGGTGGCTTGATTTTTATGCGGCTATGAC<br>TGAATTTCTTGGGTTATTTGTAGATGAAAAAAAGTAGAATAGGA<br>GTGGTTTGAGATGGTCACAAGAATAACAGGTCTGGCGTCAGGA<br>ATGGATATAGATGATATCGTATCAAAGCTGATGCAGACAGAAAG<br>AGCGCCGCTTGATAAGCTGACACAAAAAAAGCAGACTCTTGAA<br>TGGCAGCGTGACAGCTATCGTGAAGTAAACTCAAAAATAAAAG<br>AATTGCAAGATTATATGTCTAAAAATACGTTGACATATCCGAGC<br>ACGTATCAGAGCAACTGGCGTTACCCAACTTAATC [SEQ ID NO: 18] |
| | phag + AcoD | CTATGACCATGATTACGCCAAGTGAACAATGATCATTCATACGA<br>AGTACCATGGCCAAATGAACATAAAAGAAGAACAAATCATTCTT<br>TTTGAAAGCGGGATTCCAGGCTTTTTAGAAGAAAAACAGTTCGT<br>CATACTTCCGCTTTCAGAAGACTCTCCATTCGTGGCACTGCAGT<br>CCGTCACTTCAGAAAATCTTGCGTTTATCGTCGTAAGTCCGTTT<br>ATCTTTTTTAAGAATTATGAATTTGATCTTGATGAATCAACTGCT<br>GAACTTTTGGATATCGATAATATTCAAGACGTAGAAGTCATGAC<br>AATATTGACTATGGCAGAGCCATTTGAAAAGTCTACTGCGAATT<br>TATTGGCTCCCATTATTGTGAATCGCAAGAACATGATGGCTAAG<br>CAAGTCGTTTTACACGACTCCTCATATACGACAAAGCATCCGAT<br>TGGAGGAGAATCATGCTAGTTTTATCGCGGAAAATAAACGAAG<br>CGATTCAAATAGGTGCTGATATTGAAGTAAAAGTGATTGCGGTT<br>GAAGGGGATCAAGTGAAGCTTGGAATTGACGCCCCAAAGCATA<br>TTGATATTCACAGGAAAGAAATTTACTTGACCATTCAGGAAGAA<br>AATAACCGTGCAGCAGCGTTATCCAGCGATGTGATCTCCGCAT<br>TATCCTCACAAAAAAAGTGAGGATTTTTTTATTTTTGTATTAACA<br>AAATCAGAGACAATCCGATATTAATGATGTAGCCGGGAGGAGG<br>CGCAAAAGACTCAGCCAGTTACAAAATAAGGGCACAAGAACGT<br>GCCTTAACAACATATTCAGGGAGGAACAAAACAATGAATATGGC<br>TGAAATCGCCCAGCTTGGAGTCTCAAACCCGTACAAACAACAG<br>TACGAAAACTATATTGGCGGAGCTTGGGTTCCGCCGGCCGGTG<br>GCGAATACTTTGAATCTACAACGCCGATTACGGGAAAACCTTTT<br>ACAAGAGTTCCGCGCTCCGGCCAACAGGATGTGGACGCAGCG<br>TTAGATGCTGCCCATGCAGCGAAAGCTGCCTGGGCTAGAACAT<br>CAACAACGGAACGCGCCAATATTTTAAACCGCATCGCAGATCG<br>TATTGAAGCGAATTTGAAACTGCTTGCTGTCGCCGAAAGCATTG<br>ACAACGGAAAACCTGTAAGAGAAACAACGGCAGCGGATCTGCC<br>GCTTGCAGTGGACCATTTTCGTTATTTTGCAGGTTGCATCAGAG<br>CACAAGAAGGCGGCATTAGCGAAATCGATGCAGACACAATTGC<br>GTACCATTTTCATGAACCTCTGGGTGTTGTGGGCCAGATTATCC<br>CGTGGAATTTTCCTTTATTGATGGCGACGTGGAAACTGGCACC<br>GGCGCTTGCTGCCGGAAACTGTGTCGTACTTAAACCTGCAGAA<br>CAAACACCGGCGTCTATCTTAGTTTTGATGGAAGTGATTGGCG<br>ATCTGCTGCCGCCGGGCGTTGTGAATGTCATCAACGGTTTTGG<br>CTTAGAAGCTGGCAAACCTTTGGCCTCAAGCCCGCGTATTTCC<br>AAAGTAGCTTTTACGGGTGAAACAACGACAGGCCGGTTAATCA<br>TGCAATATGCATCACAGAATTTGATTCCTGTTACACTGGAACTT<br>GGCGGAAAAAGCCCGAACATTTTCTTTGAAGATGTGTTAGCAG<br>CGGATGACGCATTTTTCGACAAAGCGCTGGAAGGATTTGCAAT<br>GTTTGCGCTTAATCAAGGCGAAGTTTGCACATGTCCTTCACGTG<br>CTCTGATCCAGGAAAGCATTTATGATCGGTTTATGGAAAGAGCC<br>CTGAAACGCGTGGCTGCCATCAGACAAGGACATCCGCTTGACA<br>CGGGAACAATGATTGGTGCTCAAGCCTCTGCAGAACAGTTAGA<br>AAAAATCTTGTCCTACATTGATCTGGGCAGAAAAGAAGGAGCA<br>CAGTGCCTTACGGGTGGCGAACGCAATGTCCTGGATGGCGAC<br>CTTGCAGGCGGCTATTACGTCAAACCTACAGTATTTGCGGGAC<br>ATAACAAAATGCGCATCTTTCAAGAAGAAATTTTTGGCCCGGTC<br>GTAAGCGTTACGACATTTAAAGATGAAGAAGAAGCACTGGCTAT |

TABLE 1-continued

| Primers and constructed genes/alleles | | |
|---|---|---|
| Primer | Description | Sequence |
| | | CGCCAACGACACGTTATATGGATTGGGTGCGGGCGTTTGGACA<br>AGAGATGGAGCACGTGCGTTTCGGATGGGAAGAGGTATTCAAG<br>CTGGCCGCGTGTGGACGAATTGTTATCATGCTTACCCGGCCCA<br>TGCAGCGTTTGGCGGATATAAACAGTCTGGCATCGGACGTGAA<br>AACCATCGGATGATGTTGGATCATTACCAACAGACAAAAAATTT<br>ATTGGTTTCTTACTCCCCGAACGCGTTGGGCTTTTTCTAATTTTA<br>AAAAAGACCTTGGCGTTGCCAGGGTCTTTTAATTTAAATTTCTAT<br>CTCCTAATCATTCCTCATCCTGTCACTAACTCATGATATAATAAC<br>CGGATTCTCCACTAACTTTTTATAAATGTATTTCCATACAAGAAA<br>TCTAAAACAGAAGATTTTTTTCCAAAAATATGTGTAATCTTATCT<br>CGACTTAGTCGATATAAACGATAGATTGGGGCATAGGGGATGA<br>TCAATTGAACATTGAAAGGCTCACTACGTTACAACCTGTTTGGG<br>ATCGTTATGATACTCAAATACATAATCAGAAAGATAATGATAACG<br>AGGTTCCTGTTCATCAAGTTTCATATACCAATCTTGCTGAAATG<br>GTGGGGGAAATGAACAAGCTTTTGGAACCTTCGCAAGTTCATC<br>TGAAGTTCGAGCTTCATGACAAGTTAAATGAATACTATGTAAAG<br>GTAATAGAGGACTCTACAAATGAAGTGATCCGCGAAATTCCAC<br>CAAAACGGTGGCTTGATTTTTATGCGGCTATGACTGAATTTCTT<br>GGGTTATTTGTAGATGAAAAAAAGTAGAATAGGAGTGGTTTGAG<br>ATGGTCACAAGAATAACAGGTCTGGCGTCAGGAATGGATATAG<br>ATGATATCGTATCAAAGCTGATGCAGACAGAAAGAGCGCCGCT<br>TGATAAGCTGACACAAAAAAAGCAGACTCTTGAATGGCAGCGT<br>GACAGCTATCGTGAAGTAAACTCAAAAATAAAAGAATTGCAAGA<br>TTATATGTCTAAAAATACGTTGACATATCCGAGCACGTATCAGA<br>GCAACTGGCGTTACCCAACTTAATC [SEQ ID NO: 19] |
| | phag + AldB | CTATGACCATGATTACGCCAAGTGAACAATGATCATTCATACGA<br>AGTACCATGGCCAAATGAACATAAAAGAAGAACAAATCATTCTT<br>TTTGAAAGCGGGATTCCAGGCTTTTTAGAAGAAAAACAGTTCGT<br>CATACTTCCGCTTTCAGAAGACTCTCCATTCGTGGCACTGCAGT<br>CCGTCACTTCAGAAAATCTTGCGTTTATCGTCGTAAGTCCGTTT<br>ATCTTTTTTAAGAATTATGAATTTGATCTTGATGAATCAACTGCT<br>GAACTTTTGGATATCGATAATATTCAAGACGTAGAAGTCATGAC<br>AATATTGACTATGGCAGAGCCATTTGAAAAGTCTACTGCGAATT<br>TATTGGCTCCCATTATTGTGAATCGCAAGAACATGATGGCTAAG<br>CAAGTCGTTTTACACGACTCCTCATATACGACAAAGCATCCGAT<br>TGGAGGAGAATCATGCTAGTTTTATCGCGGAAAATAAACGAAG<br>CGATTCAAATAGGTGCTGATATTGAAGTAAAAGTGATTGCGGTT<br>GAAGGGGATCAAGTGAAGCTTGGAATTGACGCCCCAAAGCATA<br>TTGATATTCACAGGAAAGAAATTTACTTGACCATTCAGGAAGAA<br>AATAACCGTGCAGCAGCGTTATCCAGCGATGTGATCTCCGCAT<br>TATCCTCACAAAAAAAGTGAGGATTTTTTTATTTTTGTATTAACA<br>AAATCAGAGACAATCCGATATTAATGATGTAGCCGGGAGGAGG<br>CGCAAAAGACTCAGCCAGTTACAAAATAAGGGCACAAGAACGT<br>GCCTTAACAACATATTCAGGGAGGAACAAAACAATGACCAATAA<br>TCCCCCTTCAGCACAGATTAAGCCCGGCGAGTATGGTTTCCCC<br>CTCAAGTTAAAAGCCCGCTATGACAACTTTATTGGCGGCGAAT<br>GGGTAGCCCCTGCCGACGGCGAGTATTACCAGAATCTGACGC<br>CGGTGACCGGGCAGCTGCTGTGCGAAGTGGCGTCTTCGGGCA<br>AACGAGACATCGATCTGGCGCTGGATGCTGCGCACAAAGTGAA<br>AGATAAATGGGCGCACACCTCGGTGCAGGATCGTGCGGCGAT<br>TCTGTTTAAGATTGCCGATCGAATGGAACAAAACCTCGAGCTGT<br>TAGCGACAGCTGAAACCTGGGATAACGGCAAACCCATTCGCGA<br>AACCAGTGCTGCGGATGTACCGCTGGCGATTGACCATTTCCGC<br>TATTTCGCCTCGTGTATTCGGGCGCAGGAAGGTGGGATCAGTG<br>AAGTTGATAGCGAAACCGTGGCCTATCATTTCCATGAACCGTTA<br>GGCGTGGTGGGGCAGATTATCCCGTGGAACTTCCCGCTGCTG<br>ATGGCGAGCTGGAAAATGGCTCCCGCGCTGGCGGCGGGCAAC<br>TGTGTGGTGCTGAAACCCGCACGTCTTACCCCGCTTTCTGTAC<br>TGCTGCTAATGGAAATTGTCGGTGATTTACTGCCGCCGGGCGT<br>GGTGAACGTGGTCAATGGCGCAGGTGGGGTAATTGGCGAATA<br>TCTGGCGACCTCGAAACGCATCGCCAAAGTGGCGTTTACCGGC<br>TCAACGGAAGTGGGCCAACAAATTATGCAATACGCAACGCAAA<br>ACATTATTCCGGTGACGCTGGAGTTGGGCGGTAAGTCGCCAAA<br>TATCTTCTTTGCTGATGTGATGGATGAAGAAGATGCCTTTTTCG<br>ATAAAGCGCTGGAAGGCTTTGCACTGTTTGCCTTTAACCAGGG<br>CGAAGTTTGCACCTGTCCGAGTCGTGCTTTAGTGCAGGAATCT<br>ATCTACGAACGCTTTATGGAACGCGCCATCCGCCGTGTCGAAA<br>GCATTCGTAGCGGTAACCCGCTCGACAGCGTGACGCAAATGG<br>GCGCGCAGGTTTCTCACGGGCAACTGGAAACCATCCTCAACTA<br>CATTGATATCGGTAAAAAAGAGGGCGCTGACGTGCTCACAGGC<br>GGGCGGCGCAAGCTGCTGGAAGGTGAACTGAAAGACGGCTAC<br>TACCTCGAACCGACGATTCTGTTTGGTCAGAACAATATGCGGG<br>TGTTCCAGGAGGAGATTTTTGGCCCGGTGCTGGCGGTGACCA<br>CCTTCAAAACGATGGAAGAAGCGCTGGAGCTGGCGAACGATAC<br>GCAATATGGCCTGGGCGCGGGCGTCTGGAGCCGCAACGGTAA |

TABLE 1-continued

Primers and constructed genes/alleles

| Primer | Description | Sequence |
| --- | --- | --- |
| | | TCTGGCCTATAAGATGGGGCGCGGCATACAGGCTGGGCGCGT<br>GTGGACCAACTGTTATCACGCTTACCCGGCACATGCGGCGTTT<br>GGTGGCTACAAACAATCAGGTATCGGTCGCGAAACCCACAAGA<br>TGATGCTGGAGCATTACCAGCAAACCAAGTGCCTGCTGGTGAG<br>CTACTCGGATAAACCGTTGGGGCTGTTCTAATTTTAAAAAAGAC<br>CTTGGCGTTGCCAGGGTCTTTTAATTTAAATTTCTATCTCCTAAT<br>CATTCCTCATCCTGTCACTAACTCATGATATAATAACCGGATTCT<br>CCACTAACTTTTTATAAATGTATTTCCATACAAGAAATCTAAAAC<br>AGAAGATTTTTTTCCAAAAATATGTGTAATCTTATCTCGACTTAG<br>TCGATATAAACGATAGATTGGGGCATAGGGGATGATCAATTGA<br>ACATTGAAAGGCTCACTACGTTACAACCTGTTTGGGATCGTTAT<br>GATACTCAAATACATAATCAGAAAGATAATGATAACGAGGTTCC<br>TGTTCATCAAGTTTCATATACCAATCTTGCTGAAATGGTGGGGG<br>AAATGAACAAGCTTTTGGAACCTTCGCAAGTTCATCTGAAGTTC<br>GAGCTTCATGACAAGTTAAATGAATACTATGTAAAGGTAATAGA<br>GGACTCTACAAATGAAGTGATCCGCGAAATTCCACCAAAACGG<br>TGGCTTGATTTTTATGCGGCTATGACTGAATTTCTTGGGTTATTT<br>GTAGATGAAAAAAAGTAGAATAGGAGTGGTTTGAGATGGTCAC<br>AAGAATAACAGGTCTGGCGTCAGGAATGGATATAGATGATATC<br>GTATCAAAGCTGATGCAGACAGAAAGAGCGCCGCTTGATAAGC<br>TGACACAAAAAAAGCAGACTCTTGAATGGCAGCGTGACAGCTA<br>TCGTGAAGTAAACTCAAAAATAAAAGAATTGCAAGATTATATGT<br>CTAAAAATACGTTGACATATCCGAGCACGTATCAGAGCAACTG<br>GCGTTACCCAACTTAATC [SEQ ID NO: 20] |

Replacement of haq with acoD, aldB or GFP Gene

Double-stranded DNA encoding the sequence of GFP, or the aldehyde dehydrogenases AcoD (from *C. necator*) and AldB (from *E. coli*) flanked by 800 base pairs 5' and 3' of the hag gene were constructed (see table 1 for sequences). In addition, the CsrA-binding site was disrupted by specifying that each construct have a single point mutation in the 5' flanking hag homology precisely 38 base pairs 5' of the GFP/AcoD/AldB coding sequence, changing the naturally occurring "G" to an "A" ("A" mutation is highlighted in these sequences in table 2). These were ligated into pMini-MAD plasmid linearized with ZP24 and ZP25 via Gibson assembly. The resulting plasmid was transformed into *E. coli* via heat transformation. Plasmid was miniprepped using a commercially available kit, and that miniprepped plasmid was used as the DNA source to do the chromosomal modification following the same protocol as for the flgM deletion.

GFP Assay to Quantify Promoter Strength

Strains to be tested were struck out on LB plates and grown overnight at 37° C. Single colonies from overnight growth were inoculated into 3 mL of LB and 1 mM IPTG was added to induce strain of *B. subtilis* with GFP under IPTG-inducible pHyspank promoter. Strains were grown at 37° C. with shaking at 275 rpm for 7 hours. Timepoints were taken at 2.5 hours, 4 hours, 5.5 hours, and 7 hours. Timepoints were taken by pulling 200 uL of culture from each tube and spinning down at 13,000×g for 2 minutes, and then resuspending the pellet in 200 uL of PBS. These resuspensions were then aliquoted into wells of a costar black 96-well plate and read on a fluorometer (excitation 485 nm; emission 535 nm). After fluorescence reading, 100 uL of each well was taken and read for absorbance at 600 nm on a spectrophotometer to normalize the fluorescence to optical density of the culture.

For plate visualization, frozen stocks were streaked out in patches on LB plates and grown overnight at 37° C. Fluorescence was visualized with a blue LED flashlight (480 nm wavelength) and an orange filter.

HPLC Assay to Quantify ALDH Activity

Sample preparation: Single colonies from overnight growth at 37° C. on LB plates were inoculated into 4 mL of LB medium and grown at 37° C. with shaking at 275 rpm for 1.75 hours to $OD_{600}$-0.2 and then split into two tubes of 2 mL each. One tube for each strain was induced with 1 mM IPTG and the other tube was left uninduced as a control. 5 hours after induction (6.75 hours of total growth), the $OD_{600}$ was assessed (all strains were at $OD_{600}$ ~4), and 1.5 mL of the culture was spun down at 6000×G for 5 minutes and the pellet was resuspended in 200 uL of PBS. 22 uL of 2M acetaldehyde was added to each tube of cells to give a final concentration of 200 mM acetaldehyde. The tubes were then incubated at 37° C. for 30 minutes. The cells were then spun down at 20,000×G for 10 minutes at 4° C., and 150 uL of the resulting supernatant was added to 1350 uL of PBS (thus, if no acetaldehyde were lost, the final concentration should now be 20 mM). These diluted supernatants were then frozen at −20° C. in 1.5 mL microcentrifuge tubes.

Standard preparation: 168 uL of acetaldehyde was added to 1332 uL of PBS to make 2M stock and frozen at −20° C. Samples to make the standard curve for HPLC were prepared fresh the day of the experiment by diluting from this 2M stock into PBS for final concentrations of 1 mM, 2.5 mM, 5 mM, 10 mM, and 20 mM standards. Each standard was made in duplicate, with one set run before the samples and one set run after the samples. All standards and samples were then loaded into HPLC vials filled up to the neck to limit head space. Samples, but not standards, were filtered through a 0.2 um filter to remove any residual bacteria when loaded into the HPLC vials.

Samples were run on a Shimadzu system with an Aminex HPX-87H column. Samples were run at 0.6 mL/min flow rate and isocratic elution with 0.005M sulfuric acid mobile phase at 50° C. (column temp). Samples were detected via refractive index.

Qualitative Analysis of AcoD Expression (Coomassie Stain)

Single colonies from overnight growth at 37° C. on LB plates were inoculated into 2.5 mL of LB medium (+1 mM IPTG for strains with pHyspank promoter) and grown at 37° C. with shaking at 275 rpm for 4.5 hours. 1.5 mL of each culture was spun down at 13,000×G for 2 minutes and the pellet was resuspended in 50 uL of lysis buffer (20 mM TRIS, 10 mM EDTA, 0.1% lysozyme, 0.01% RNaseA, 0.002% DNasel, and Roche EDTA-free cOmplete protease inhibitor cocktail tablet diluted per manufacturer specifications). Samples were then incubated in lysis buffer for 30 minutes in 37° C. water bath. 50 uL of 2× laemmli buffer was then added to samples and the samples were incubated at 100° C. on a thermocycler for 5 minutes. Samples were then spun down at 13,000×G for 2 minutes and 10 uL were loaded onto an 8% SDS-PAGE gel and run at 140V for 1 hour. The gel was then rinsed with ddH2O 6 times with shaking for 5 minutes each. It was then incubated in Coomassie brilliant blue stain overnight at room temperature with shaking.

Results:

Expression of ALDH Genes Heterologously in *B. subtilis* Results in Physiologically Relevant Rates of Acetaldehyde Breakdown.

To assess the ability of *B. subtilis* to heterologously express a functional acetaldehyde dehydrogenase, a strain encoding an acetaldehyde dehydrogenase gene under the control of a pHyspank promoter, which is IPTG inducible was constructed. Two different acetaldehyde dehydrogenases were selected after review of the literature. The criteria for selection were: characterized enzyme kinetics and high specificity for acetaldehyde; bacterial origin; from a non-pathogenic bacteria; soluble protein product (i.e. not membrane-bound); and amino acid sequence known. After conducting such a search, several candidates were identified, and two were selected as best fits in these criteria. The first was AcoD, encoded by the acoD gene from *C. necator* [12], which has an experimentally determined Km for acetaldehyde of ~4 uM, and uses NAD as its co-factor for oxidizing acetaldehyde to acetate. The second was AldB, encoded by the aldB gene of *E. coli* [13], which has an experimentally determined Km of ~2.5 uM and a Vmax of 2 U/mg, and uses NADP as its co-factor.

*B. subtilis* with acoD under control of the pHyspank promoter and *B. subtilis* with aldB under control of the pHyspank promoter were grown with and with IPTG induction and then incubated with 200 mM IPTG for 30 minutes at room temperature. The samples were then filtered to remove all bacteria and frozen at −20° C.

Samples were thawed and diluted 1:10 in PBS and standards were prepared freshly the day of the HPLC assay. All samples were then run on an HPLC to quantify the amount of acetaldehyde. In addition to running two sets of standards, one at the beginning and one at the end of the run, a single preparation of a 10 mM standard of acetaldehyde was run at the beginning and the end of the run (i.e. the same tube run twice) to control for any potential evaporation or other stochastic loss of acetaldehyde during the HPLC run, since the tubes would be on the machine for several hours and it was desired to ensure that samples run later in the order would not erroneously appear lower. A standard curve was generated based on area under the curve for each standard sample, and the best-fit line had an $R^2$ of >0.99. The equation for this line was then used to generate concentrations for each of the samples. The results of this assay are presented in FIG. 1. There was essentially no difference in the acetaldehyde standard run twice, indicating no significant stochastic loss of acetaldehyde from the samples during the run. In addition, the samples with uninduced bacteria had acetaldehyde levels that corresponded nicely with the 20 mM standard, demonstrating that the uninduced bacteria do not effectively remove acetaldehyde by naturally occurring mechanisms.

However, when AldB or AcoD were induced, the samples showed a reduction of ~4 mM and ~8 mM (respectively) in acetaldehyde concentration, indicating that induction of the protein caused removal of acetaldehyde.

Combination of flgM Deletion and CsrA-Binding Site Point Mutation Results in Robust and Constitutive Heterologous Protein Expression Via the Haq Promoter.

Flagellin, encoded by the hag gene in *B. subtilis*, is expressed at extremely high levels when the cell determines that motility is advantageous. However, because the manufacture of a flagellum is very nutritionally and energetically expensive for the cell, it has several mechanisms to repress production of Hag at times in the life cycle when motility would be inappropriate.

FlgM is known to bind and repress the sigma factor SigD that activates transcription of hag. Thus, deletion of flgM should remove transcriptional repression and result in high levels of expression constitutively. hag translation into protein is further repressed post-transcriptionally by CsrA, which binds to hag transcripts at the ribosome binding site, thus competitively inhibiting ribosome translation. A single point mutation in this binding site precludes CsrA binding, but not ribosome binding, thus allowing for constitutive translation of hag transcript.

Figure 2A:
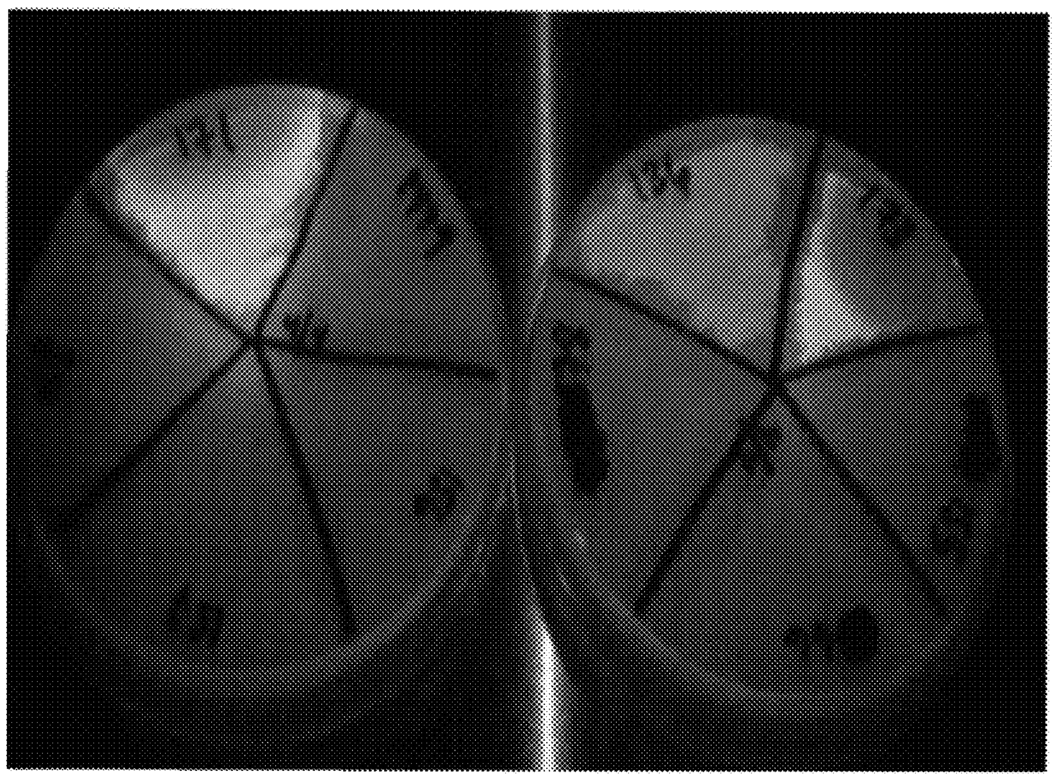
FIG. 2 shows expression of GFP is 5-10 times stronger under control of the modified hag promoter than under the control of pHyspank promoter. (A) Frozen stocks of *Bacillus subtilis* strain PY79 (negative control; left plate at "2-o'clock" position), *B. subtilis* expressing GFP under pHyspank promoter with lacl repression removed (right plate at "11-o'clock" position), and *B. subtilis* expressing GFP under the modified hag promoter (left plate at "11-o'clock" position, and right plate at "2-o'clock" position) were patched on LB and grown overnight. The green fluorescence was visualized with a blue LED flashlight and orange filter. (B) Cultures of *B. subtilis* expressing GFP under pHyspank promoter with lacl repression removed (dark grey bottom line in chart; right plate at "11-o'clock" position in (A)), and *B. subtilis* expressing GFP under the modified hag promoter (light grey top line in graph; left plate at "11-o'clock" position in (A)) were grown from individual colonies in LB broth for 7 hours and fluorescence and $OD_{600}$ readings were taken every 90 minutes starting at 2.5 hours.

To test the hypothesis that removal of these two key mechanisms of repression would result in robust and constitutive expression of a heterologous protein, flgM was deleted, a single point mutation was made in the CsrA-binding site, and the hag gene was replaced with a reporter of expression, GFP. The fluorescence of this strain on a plate was compared to that of a strain expressing GFP via the de-repressed pHyspank promoter (lacl was deleted from this construct to ensure constitutive expression, and the delta lacl strain was shown to have similar levels of GFP expression to a strain with lacl intact and induced with 1 mM IPTG [data not shown]). When struck out side by side, two different isolates of the modified hag expression system were qualitatively much brighter than the pHyspank expression system (FIG. 2*a*).

Figure 2B:
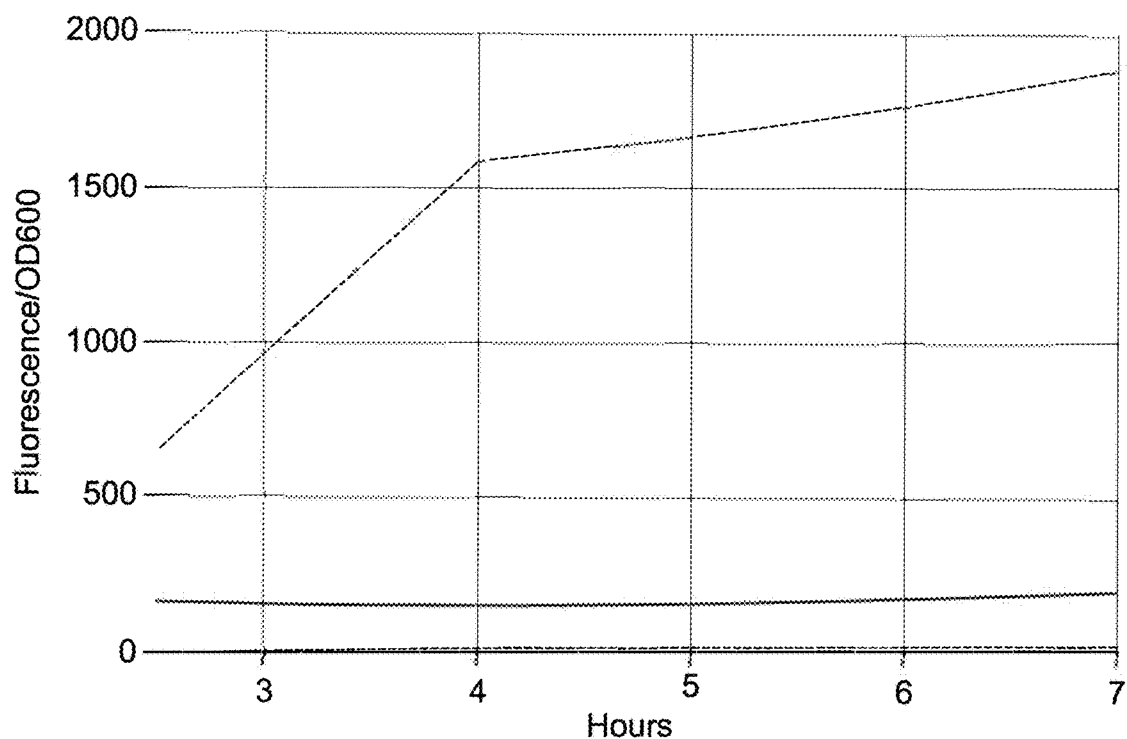

However, to see if expression was indeed constitutive, and to quantify the difference between these two expression systems, a broth growth and fluorescence time course was taken. Strains were grown in LB, and the $OD_{600}$ and fluorescence were assessed at 2.5 hours of growth, and then every 90 minutes thereafter up to 7 hours (FIG. 2*b*). Indeed, after 2.5 hours the fluorescence normalized to $OD_{600}$ was ~4 times higher in the modified hag expression system than in the pHyspank expression system. This increased to ~10 times higher by 4 hours and remained ~10 times higher through the 7 hours assessed.

Utilizing the De-Repressed hag Promoter, Qualitatively Higher Levels of AcoD are Produced than by pHyspank.

Figure 3:
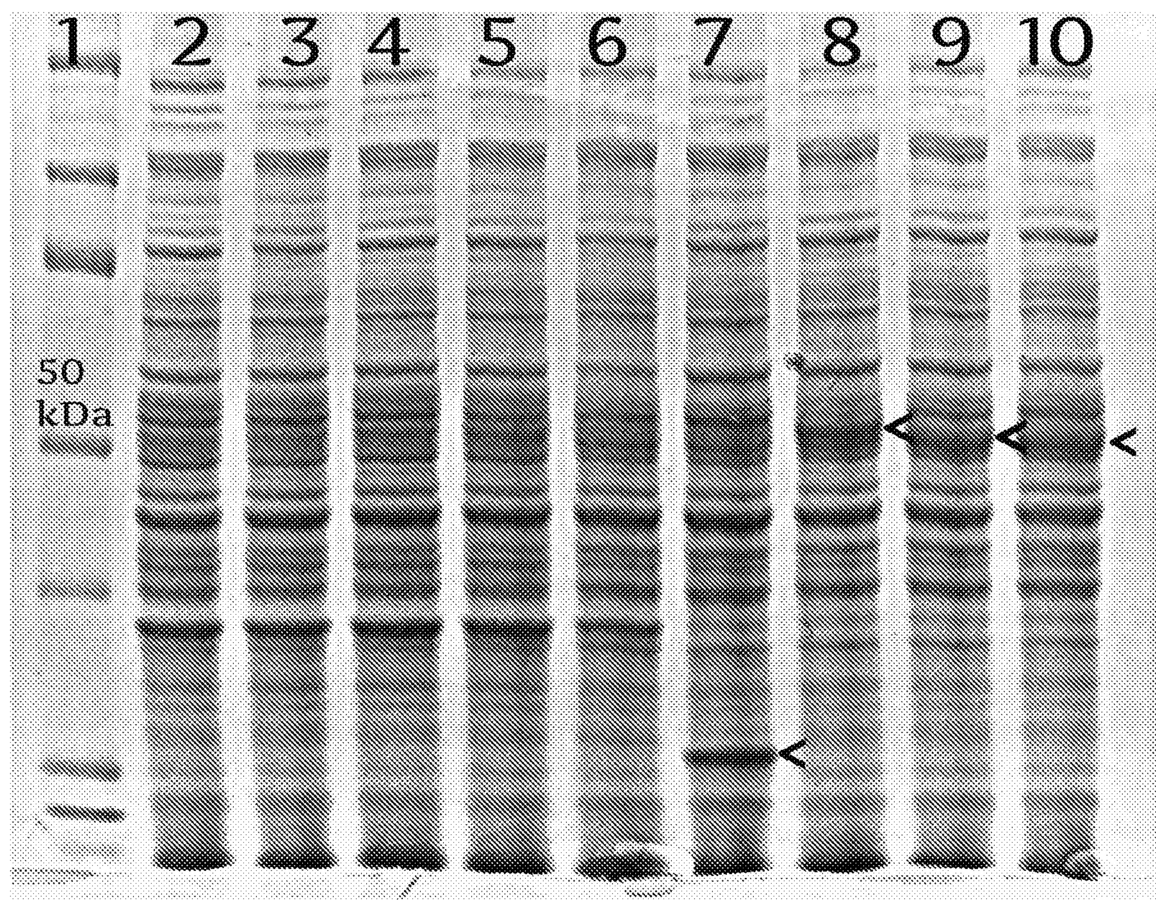
FIG. 3 shows expression of GFP, AcoD, and AldB by presence of protein in pelleted cells from cultures grown for 4.5 hours in LB, lysed and assessed for total protein by Coomassie staining on 8% SDS-PAGE gel. Lane 1 is the Bio-Rad Kaleidoscope protein standard ladder. Lanes 2 and 3 are uninduced and induced cultures (respectively) of *B.*

To ensure robust and constitutive expression via our modified hag promoter was not specific to GFP but could be utilized for other heterologous protein expression, including aldehyde dehydrogenases, two different aldehyde dehydrogenase genes were inserted into the hag locus of two different strains: acoD from *C. necator* and aldB from *E. coli*. These strains were then grown up in broth culture along with strains expressing acoD and aldB via the pHyspank promoter and a strain expressing GFP via the modified hag promoter as a positive control. The bacteria were pelleted and lysed and lysates were run on an SDS-PAGE gel and stained for total protein using Coomassie. As expected, there is an obvious band for GFP (FIG. 3). In addition, there are equally bright bands for his-tagged AcoD, untagged AcoD, and his-tagged AldB when expressed via the modified hag promoter (FIG. 3). However, there are only faint bands of the expected size for AcoD and AldB under induced pHyspank control. Despite this apparently low level of expression, it is known from the HPLC experiment that this level is sufficient for removal of acetaldehyde at physiologically relevant rates. Thus, as the Coomassie staining demonstrates that there is qualitatively obviously more protein being produced via the modified hag promoter, it is reasonable to expect that this expression system would produce at least as robust a rate of acetaldehyde removal, if not much more.

Discussion:

Enzymatic approaches are rapidly replacing small molecules and becoming the standard in the pharmaceutical world in large part due to their superior efficacy, versatility, and specificity. Evidence of this can be seen in the fact that the biologics drug market was, in 2017, worth over $200B and set to double in the next seven years. In addition, 8 of the top 10 best-selling drugs in 2016 were biologics.

However, the current process to make biologic drugs is long, expensive, and generally approached with a mindset similar to that used to manufacture small molecule drugs. A stepwise change in method is necessary in order to make this powerful class of drug available for broader uses. The purpose of this invention is to make a cost-effective, orally deliverable enzymatic therapy for the alcohol hangover.

Figure 1:
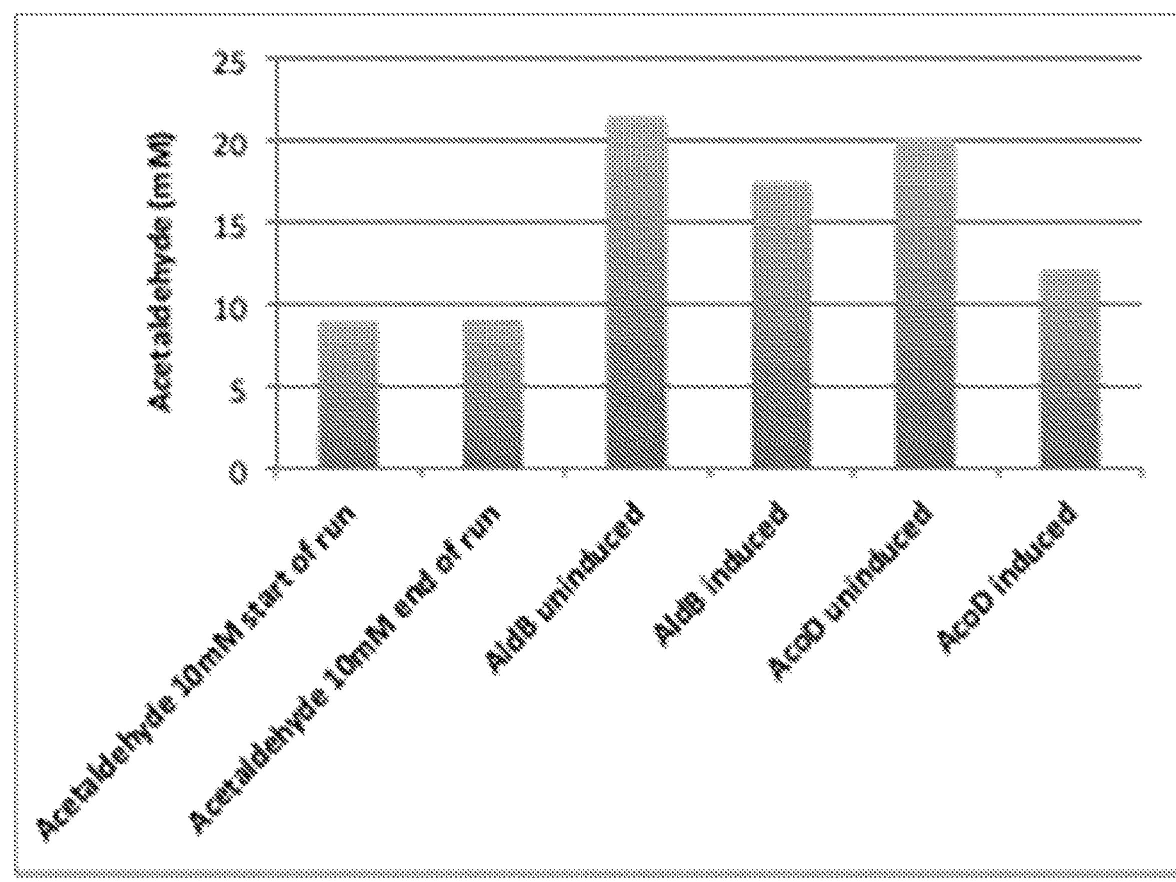
FIG. 1 shows that induction of the aldehyde dehydrogenases AldB or AcoD results in rapid removal of acetaldehyde. Samples were incubated for 30 minutes with 200 mM acetaldehyde at 37° C. Samples were then filtered, diluted 1:10, and frozen. Thawed samples were then run on HPLC and compared to a standard curve to calculate remaining acetaldehyde concentration, and those values are presented here. "Acetaldehyde 10 mM" refers to 10 mM acetaldehyde standard that was run at the start of the HPLC run, and then again at the end of the HPLC run to ensure no stochastic loss of acetaldehyde while on the machine.

As demonstrated in FIG. 1, intracellular expression of two different heterologous proteins resulted in marked removal of acetaldehyde. Indeed, if one assumes that a heavy night of drinking causes a colonic acetaldehyde level of ~150 uM [14], and there are approximately 15 L of extracellular fluid in a 72 kg human body, then the same amount of bacteria could remove 150 uM of acetaldehyde from 15 L in roughly 3 hours. While of course this is a "back-of-the-envelop" calculation, it is at least not unreasonable to assume that these could represent relatively physiologically relevant rates.

In addition, the no-bacterial control demonstrates that the drop was not due to simple evaporation or some other method of removal, and the uninduced controls demonstrate that the removal was specific to expression of the ALDH and not some inherent function of the bacteria. Furthermore, the re-reading of the same 20 mM standard tube at the beginning and end of the run demonstrate that any drop was not due to evaporation during the HPLC run. Also, the removal of acetaldehyde was dependent on induction of the aldehyde dehydrogenases, indicating that the bacteria do not naturally remove acetaldehyde on their own, but require the heterologously expressed acetaldehyde dehydrogenase.

By removing FlgM and CsrA repression, rapid and robust expression of GFP constitutively was achieved throughout the growth cycle of our strain. The fact that these levels are 5-10 times higher than the expression levels using the pHyspank promoter—an academic gold standard for expression in *B. subtilis*—demonstrates the utility of the expression system. Furthermore, it is also important to note that the fluorescence/$OD_{600}$ ratio continued to increase throughout the entire growth curve, indicating that the fluorescence was increasing faster than the OD, meaning that each cell was continuing to produce more GFP. This is consistent with the hypothesis that the flgM deletion and CsrA-binding site mutation result in constitutive and robust expression. Had the expression not been constitutive throughout the growth curve the ratio of fluorescence to $OD_{600}$ would have eventually plateaued or dropped, even if the absolute fluorescence continued to rise.

In addition, the demonstration of physiologically relevant rates of acetaldehyde removal was done using the pHyspank promoter, indication that our system utilizing the edited pHag promoter generates more protein and should even more sufficiently exceed necessary rates of acetaldehyde removal. Indeed, qualitative comparisons of band densities of AcoD in a Coomassie gel (FIG. 2*b*) demonstrate a much more robust protein band indicating far superior protein expression.

Taken together, a novel system for acetaldehyde removal from the body has been developed that is distinct from any other strategy currently described or executed. It involves edible bacteria engineered to express heterologous protein constitutively for the purpose of enzymatically removing acetaldehyde directly. It utilizes a heterologous protein expression strategy that takes advantage of the robust flagellin promoter, enhanced by removal of repressors of that promoter.

Example 2

A subject ingests a water suspension of 1E9 CFU of a spore preparation *B. subtilis* with the following modifications: FlgM deleted, a mutation in BS1 as described herein and the hag gene replaced with AcoD as described herein. Immediately following this, the person ingests six alcoholic beverages (12 ounces of 5% ethanol) over the next 3 hours before going to bed. Typically, this amount of alcohol results in this person having an alcohol hangover characterized by: grogginess, severe headache, nausea, malaise, sensitivity to light and sound, vertigo, and irritability. These symptoms typically set in within the 8 hours while the person sleeps and persist for 12 hours thereafter. However, the person awakens 8 hours later with none of the excess acetaldehyde formed by his or her body due to the metabolism of the ethanol consumed the night before. Thus, while he or she has mild grogginess and a slight headache due to dehydration, the person has greatly reduced or none of the other symptoms associated with a hangover.

Exemplary Embodiments

1. A method for preventing or treating an alcohol hangover, comprising administering to the gut of a subject in need thereof an effective amount of a composition comprising a recombinant bacterium recombinantly engineered to constitutively express an aldehyde dehydrogenase.

2. The method of embodiment 1, wherein the recombinant bacteria comprises: a) a polynucleotide comprising an expression construct comprising a flagellin gene promoter operatively linked with a heterologous nucleotide sequence encoding an aldehyde dehydrogenase, wherein the flagellin gene promoter comprises one or more genetic modifications that reduce CsrA repression of translation of an mRNA transcribed from the flagellin gene promoter; and b) a genetic modification of a sigma factor repressor, wherein the modification reduces inhibition of sigma factor initiation of transcription from the flagellin gene promoter.

3. The method of embodiment 2, wherein the bacterium belongs to a genus selected from *Bacillus, Bifidobacterium, Enterococcus, Escherichia, Lactobacillus, Leuconostoc, Pediococcus, Pediococcus* and *Streptococcus.*

4. The method of embodiment 2, wherein (1) the bacterium belongs to genus *Bacillus*, (2) the flagellin gene promoter is a modified *Bacillus* hag promoter comprising one or more genetic modifications of the CsrA BS1 binding site and/or the CsrA BS2 binding site, (3) the sigma factor is SigD and (4) the SigD repressor is FlgM.

5. The method of embodiment 4, wherein the hag promoter comprises one or more genetic modifications in the 12-base-pair BS1 binding site or in the surrounding bases on either side of the binding site that form the stem of the stem-loop secondary structure of BS1.

6. The method of embodiment 4, wherein the hag promoter comprises a modification of the CsrA BS1 recognition sequence, AGGA.

7. The method of embodiment 4, wherein the hag promoter comprises the nucleotide sequence GCACAAGAACGT [SEQ ID NO:2].

8. The method of embodiment 4, wherein the one or more genetic modifications comprise one or more point mutations to the CsrA BS2 binding site.

9. The method of embodiment 4, wherein the hag promoter comprises one or more genetic modifications that disrupt the stem and loop structure of BS2 by eliminating complementarity that allows hydrogen bonding.

10. The method of embodiment 4, wherein the hag promoter comprises a modification of the BS2 binding site, wherein the modification comprises the nucleotide sequence ATTTAGGGAGGAA [SEQ ID NO:3].

11. The method of embodiment 1, wherein the aldehyde dehydrogenase is a bacterial aldehyde dehydrogenase.

12. The method of embodiment 4, wherein the aldehyde dehydrogenase is selected from (1) AcoD from *Cupriavidus* necator and (2) AldB from *E. coli.*

13. The method of embodiment 4, wherein the genetic modification in a flgM gene comprises deletion of all or part of the flgM gene.

14. The method of embodiment 4, wherein the genetic modification in a flgM gene disrupts secondary or tertiary structure.

15. The method of embodiment 4, wherein the expression construct is located in a bacterial chromosome.

16. The method of embodiment 1, comprising administering the composition to the subject during consumption of alcohol.

17. The method of embodiment 1, comprising administering the composition to the subject up to 24 hours before commencement of consumption of alcohol.

18. The method of embodiment 1, wherein the composition is administered orally.

19. The method of embodiment 1, wherein the composition further comprises a physiologically acceptable carrier selected from lactic acid fermented foods, fermented dairy products, resistant starch, dietary fibers, carbohydrates, proteins and glycosylated proteins, water, capsule filler, and a gummy material.

20. The method of embodiment 1, wherein the composition comprises about $10^4$ to about $10^{12}$ colony forming units of the recombinant bacteria.

BIBLIOGRAPHY

1. Sprince, H., et al., *Protective action of ascorbic acid and sulfur compounds against acetaldehyde toxicity: implications in alcoholism and smoking*. Agents Actions, 1975. 5(2): p. 164-73.
2. Mukherjee, S. and D. B. Kearns, *The structure and regulation of flagellin Bacillus subtilis*. Annu Rev Genet, 2014. 48: p. 319-40.
3. Guttenplan, S. B., S. Shaw, and D. B. Kearns, *The cell biology of peritrichous flagellin Bacillus subtilis*. Mol Microbiol, 2013. 87(1): p. 211-29.
4. Macnab, R. M., *Genetics and biogenesis of bacterial flagella*. Annu Rev Genet, 1992. 26: p. 131-58.
5. Caramori, T., et al., *Role of FlgM in sigma D-dependent gene expression in Bacillus subtilis*. J Bacteriol, 1996. 178(11): p. 3113-8.
6. Yakhnin, H., et al., *CsrA of Bacillus subtilis regulates translation initiation of the gene encoding the flagellin protein (hag) by blocking ribosome binding*. Mol Microbiol, 2007. 64(6): p. 1605-20.
7. Mukherjee, S., et al., *CsrA-FliW interaction governs flagellin homeostasis and a checkpoint on flagellar morphogenesis in Bacillus subtilis*. Mol Microbiol, 2011. 82(2): p. 447-61.
8. Vakulskas, C. A., et al., *Regulation of bacterial virulence by Csr (Rsm) systems*. Microbiol Mol Biol Rev, 2015. 79(2): p. 193-224.
9. Chen, R., et al., *Role of the sigmaD-dependent autolysins in Bacillus subtilis population heterogeneity*. J Bacteriol, 2009. 191(18): p. 5775-84.
10. Ben-Yehuda, S., D. Z. Rudner, and R. Losick, *RacA, a bacterial protein that anchors chromosomes to the cell poles*. Science, 2003. 299(5606): p. 532-6.
11. Gibson, D. G., et al., *Enzymatic assembly of DNA molecules up to several hundred kilobases*. Nat Methods, 2009. 6(5): p. 343-5.
12. Jendrossek, D., A. Steinbuchel, and H. G. Schlegel, *Three different proteins exhibiting NAD-dependent acetaldehyde dehydrogenase activity from Alcaligenes eutrophus*. Eur J Biochem, 1987. 167(3): p. 541-8.
13. Ho, K. K. and H. Weiner, *Isolation and characterization of an aldehyde dehydrogenase encoded by the aldB gene of Escherichia coli*. J Bacteriol, 2005. 187(3): p. 1067-73.
14. Salaspuro, M., *Microbial metabolism of ethanol and acetaldehyde and clinical consequences*. Addict Biol, 1997. 2(1): p. 35-46.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or."

While embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. A composition comprising a recombinant bacterium engineered to comprise:

a) a polynucleotide comprising an expression construct comprising a flagellin gene promoter operatively linked with a heterologous nucleotide sequence, wherein the heterologous nucleotide sequence encodes an aldehyde dehydrogenase, wherein the flagellin gene promoter comprises one or more genetic modifications that reduce Carbon storage regulator A ("CsrA") repression of translation of an mRNA transcribed from the flagellin gene promoter; and b) a genetic modification of a sigma factor repressor, wherein the modification reduces inhibition of sigma factor initiation of transcription from the flagellin gene promoter.

2. The composition of claim 1, wherein the bacterium belongs to a genus selected from *Bacillus, Bifidobacterium, Enterococcus, Escherichia, Lactobacillus, Leuconostoc, Pediococcus*, and *Streptococcus*.

3. The composition of claim 1, wherein (1) the bacterium belongs to genus *Bacillus*, (2) the flagellin gene promoter is a modified *Bacillus* hag promoter comprising one or more genetic modifications of the CsrA BS1 binding site and/or the CsrA BS2 binding site, (3) the sigma factor is SigD, and (4) the sigma factor repressor is FlgM.

4. The composition of claim 3, wherein the modified *Bacillus* hag promoter comprises one or more genetic modifications in the 12-base-pair BS1 binding site or in the surrounding bases on either side of the binding site that form the stem of the stem-loop secondary structure of BS1.

5. The composition of claim 3, wherein the modified *Bacillus* hag promoter comprises a modification of the CsrA BS1 recognition sequence, AGGA.

6. The composition of claim 3, wherein the modified *Bacillus* hag promoter comprises the nucleotide sequence GCACAAGAACGT (SEQ ID NO:2).

7. The composition of claim 3, wherein the one or more genetic modifications comprise one or more point mutations to the CsrA BS2 binding site.

8. The composition of claim 3, wherein the modified *Bacillus* hag promoter comprises one or more genetic modifications that disrupt the stem and loop structure of BS2 by eliminating complementarity that allows hydrogen bonding.

9. The composition of claim 3, wherein the modified *Bacillus* hag promoter comprises a modification of the BS2 binding site, wherein the modification comprises the nucleotide sequence ATTTAGGGAGGAA (SEQ ID NO:3).

10. The composition of claim 3, wherein the genetic modification in a flgM gene comprises deletion of all or part of the flgM gene.

11. The composition of claim 3, wherein the genetic modification in a flgM gene disrupts secondary or tertiary structure.

12. The composition of claim 3, wherein the expression construct is located in a bacterial chromosome.

13. The composition of claim 1, wherein the aldehyde dehydrogenase is selected from (1) AcoD from *Cupriavidus necator* and (2) AldB from *E. coli*.

14. The composition of claim 1, wherein the composition is formulated for oral administration.

15. The composition of claim 1, wherein the composition further comprises a physiologically acceptable carrier selected from lactic acid fermented foods, fermented dairy products, resistant starch, dietary fibers, carbohydrates, proteins and glycosylated proteins, water, capsule filler, and a gummy material.

16. The composition of claim 1, wherein the composition comprises about $10^4$ to about $10^{12}$ colony forming units of the recombinant bacteria.

* * * * *

SEQUENCE LISTING

```
<160> NUMBER OF SEQ ID NOS: 22

<210> SEQ ID NO 1
<211> LENGTH: 23
<212> TYPE: DNA
<213> ORGANISM: Bacillus subtilis

<400> SEQUENCE: 1

taagggcaca aggacgtgcc tta                                                23


<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gcacaagaac gt                                                            12


<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

atttagggag gaa                                                           13


<210> SEQ ID NO 4
<211> LENGTH: 506
<212> TYPE: PRT
<213> ORGANISM: Cupriavidus necator

<400> SEQUENCE: 4

Met Asn Met Ala Glu Ile Ala Gln Leu Gly Val Ser Asn Pro Tyr Lys
1               5                   10                  15

Gln Gln Tyr Glu Asn Tyr Ile Gly Gly Ala Trp Val Pro Pro Ala Gly
            20                  25                  30

Gly Glu Tyr Phe Glu Ser Thr Thr Pro Ile Thr Gly Lys Pro Phe Thr
        35                  40                  45

Arg Val Pro Arg Ser Gly Gln Gln Asp Val Asp Ala Ala Leu Asp Ala
    50                  55                  60

Ala His Ala Ala Lys Ala Ala Trp Ala Arg Thr Ser Thr Thr Glu Arg
65                  70                  75                  80

Ala Asn Ile Leu Asn Arg Ile Ala Asp Arg Ile Glu Ala Asn Leu Lys
                85                  90                  95

Leu Leu Ala Val Ala Glu Ser Ile Asp Asn Gly Lys Pro Val Arg Glu
            100                 105                 110

Thr Thr Ala Ala Asp Leu Pro Leu Ala Val Asp His Phe Arg Tyr Phe
        115                 120                 125

Ala Gly Cys Ile Arg Ala Gln Glu Gly Gly Ile Ser Glu Ile Asp Ala
    130                 135                 140

Asp Thr Ile Ala Tyr His Phe His Glu Pro Leu Gly Val Val Gly Gln
```

```
145                 150                 155                 160

Ile Ile Pro Trp Asn Phe Pro Leu Leu Met Ala Thr Trp Lys Leu Ala
                165                 170                 175

Pro Ala Leu Ala Ala Gly Asn Cys Val Val Leu Lys Pro Ala Glu Gln
            180                 185                 190

Thr Pro Ala Ser Ile Leu Val Leu Met Glu Val Ile Gly Asp Leu Leu
        195                 200                 205

Pro Pro Gly Val Val Asn Val Ile Asn Gly Phe Gly Leu Glu Ala Gly
    210                 215                 220

Lys Pro Leu Ala Ser Ser Pro Arg Ile Ser Lys Val Ala Phe Thr Gly
225                 230                 235                 240

Glu Thr Thr Thr Gly Arg Leu Ile Met Gln Tyr Ala Ser Gln Asn Leu
                245                 250                 255

Ile Pro Val Thr Leu Glu Leu Gly Gly Lys Ser Pro Asn Ile Phe Phe
            260                 265                 270

Glu Asp Val Leu Ala Ala Asp Asp Ala Phe Phe Asp Lys Ala Leu Glu
        275                 280                 285

Gly Phe Ala Met Phe Ala Leu Asn Gln Gly Glu Val Cys Thr Cys Pro
    290                 295                 300

Ser Arg Ala Leu Ile Gln Glu Ser Ile Tyr Asp Arg Phe Met Glu Arg
305                 310                 315                 320

Ala Leu Lys Arg Val Ala Ala Ile Arg Gln Gly His Pro Leu Asp Thr
                325                 330                 335

Gly Thr Met Ile Gly Ala Gln Ala Ser Ala Glu Gln Leu Glu Lys Ile
            340                 345                 350

Leu Ser Tyr Ile Asp Leu Gly Arg Lys Glu Gly Ala Gln Cys Leu Thr
        355                 360                 365

Gly Gly Glu Arg Asn Val Leu Asp Gly Asp Leu Ala Gly Gly Tyr Tyr
    370                 375                 380

Val Lys Pro Thr Val Phe Ala Gly His Asn Lys Met Arg Ile Phe Gln
385                 390                 395                 400

Glu Glu Ile Phe Gly Pro Val Val Ser Val Thr Thr Phe Lys Asp Glu
                405                 410                 415

Glu Glu Ala Leu Ala Ile Ala Asn Asp Thr Leu Tyr Gly Leu Gly Ala
            420                 425                 430

Gly Val Trp Thr Arg Asp Gly Ala Arg Ala Phe Arg Met Gly Arg Gly
        435                 440                 445

Ile Gln Ala Gly Arg Val Trp Thr Asn Cys Tyr His Ala Tyr Pro Ala
    450                 455                 460

His Ala Ala Phe Gly Gly Tyr Lys Gln Ser Gly Ile Gly Arg Glu Asn
465                 470                 475                 480

His Arg Met Met Leu Asp His Tyr Gln Gln Thr Lys Asn Leu Leu Val
                485                 490                 495

Ser Tyr Ser Pro Asn Ala Leu Gly Phe Phe
            500                 505
```

<210> SEQ ID NO 5
<211> LENGTH: 517
<212> TYPE: PRT
<213> ORGANISM: Homo sapiens

<400> SEQUENCE: 5

```
Met Leu Arg Ala Ala Ala Arg Phe Gly Pro Arg Leu Gly Arg Arg Leu
1               5                   10                  15
```

-continued

```
Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
        35                  40                  45

Val Ser Arg Lys Thr Phe Pro Thr Val Asn Pro Ser Thr Gly Glu Val
    50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285

Lys Ser Pro Asn Ile Ile Met Ser Asp Ala Asp Met Asp Trp Ala Val
    290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
        355                 360                 365

Lys Ile Leu Gly Tyr Ile Asn Thr Gly Lys Gln Glu Gly Ala Lys Leu
    370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
```

```
        435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Glu Val Lys Thr Val Thr Val Lys Val
            500                 505                 510

Pro Gln Lys Asn Ser
        515


<210> SEQ ID NO 6
<211> LENGTH: 915
<212> TYPE: DNA
<213> ORGANISM: Bacillus subtilis

<400> SEQUENCE: 6

atgagaatta accacaatat tgcagcgctt aacacactga accgtttgtc ttcaaacaac      60

agtgcgagcc aaaagaacat ggagaaactt tcttcaggtc ttcgcatcaa ccgtgcggga     120

gatgacgcag caggtcttgc gatctctgaa aaaatgagag gacaaatcag aggtcttgaa     180

atggcttcta aaaactctca agacggaatc tctcttatcc aaacagctga gggtgcatta     240

actgaaactc atgcgatcct tcaacgtgtt cgtgagctag ttgttcaagc tggaaacact     300

ggaactcagg acaaagcaac tgatttgcaa tctattcaag atgaaatttc agctttaaca     360

gatgaaatcg atggtatttc aaatcgtaca gaattcaatg gtaagaaatt gctcgatggc     420

acttacaaag ttgacacagc tactcctgca aatcaaaaga acttggtatt ccaaatcgga     480

gcaaatgcta cacagcaaat ctctgtaaat attgaggata tgggtgctga cgctcttgga     540

attaaagaag ctgatggttc aattgcagct cttcattcag ttaatgatct tgacgtaaca     600

aaattcgcag ataatgcagc agatactgct gatatcggtt tcgatgctca attgaaagtt     660

gttgatgaag cgatcaacca agtttcttct caacgtgcta agcttggtgc ggtacaaaat     720

cgtctagagc acacaattaa caacttaagc gcttctggtg aaaacttgac agctgctgag     780

tctcgtatcc gtgacgttga catggctaaa gagatgagcg aattcacaaa gaacaacatt     840

ctttctcagg cttctcaagc tatgcttgct caagcaaacc aacagccgca aaacgtactt     900

caattattac gttaa                                                      915


<210> SEQ ID NO 7
<211> LENGTH: 276
<212> TYPE: DNA
<213> ORGANISM: Bacillus subtilis

<400> SEQUENCE: 7

ggaattgacg ccccaaagca tattgatatt cacaggaaag aaatttactt gaccattcag      60

gaagaaaata accgtgcagc agcgttatcc agcgatgtga tctccgcatt atcctcacaa     120

aaaaagtgag gattttttta tttttgtatt aacaaaatca gagacaatcc gatattaatg     180

atgtagccgg gaggaggcgc aaaagactca gccagttaca aaataagggc acaaggacgt     240

gccttaacaa catattcagg gaggaacaaa acaatg                               276


<210> SEQ ID NO 8
<211> LENGTH: 12
<212> TYPE: DNA
```

<213> ORGANISM: Bacillus subtilis

<400> SEQUENCE: 8
gcacaaggac gt 12

<210> SEQ ID NO 9
<211> LENGTH: 13
<212> TYPE: DNA
<213> ORGANISM: Bacillus subtilis

<400> SEQUENCE: 9
attcagggag gaa 13

<210> SEQ ID NO 10
<211> LENGTH: 225
<212> TYPE: DNA
<213> ORGANISM: Bacillus subtilis

<400> SEQUENCE: 10
atgctagttt tatcgcggaa aataaacgaa gcgattcaaa taggtgctga tattgaagta 60
aaagtgattg cggttgaagg ggatcaagtg aagcttggaa ttgacgcccc aaagcatatt 120
gatattcaca ggaaagaaat ttacttgacc attcaggaag aaaataaccg tgcagcagcg 180
ttatccagcg atgtgatctc cgcattatcc tcacaaaaaa agtga 225

<210> SEQ ID NO 11
<211> LENGTH: 267
<212> TYPE: DNA
<213> ORGANISM: Bacillus subtilis

<400> SEQUENCE: 11
atgaaaatca atcaatttgg aacacaatcc gttaatccat atcaaaaaaa ttatgataag 60
caagcggtgc aaaaaactgt tgcacaacct caagataaaa ttgaaatttc atcacaggct 120
aaagaaatgc aacatgcatc cgacgcagtc actggttcac gacaggaaaa aattgcgcag 180
cttaaagcgc aaattgaaaa cgggtcatac aaagtagacg caaatcatat tgcgaaaaat 240
atgattaatt tttataaaaa gcaataa 267

<210> SEQ ID NO 12
<211> LENGTH: 765
<212> TYPE: DNA
<213> ORGANISM: Bacillus subtilis

<400> SEQUENCE: 12
atgcaatcct tgaattatga agatcaggtg ctttggacgc gctggaaaga gtggaaagat 60
cctaaagccg gtgacgactt aatgcgccgt tacatgccgc ttgtcacata tcatgtaggc 120
agaatttctg tcggactgcc gaaatcagtg cataaagacg atcttatgag ccttggtatg 180
cttggtttat atgatgccct tgaaaaattt gaccccagcc gggacttaaa atttgatacc 240
tacgcctcgt ttagaattcg cggcgcaatc atagacgggc ttcgtaaaga agattggctg 300
cccagaacct cgcgcgaaaa aacaaaaaag gttgaagcag caattgaaaa gcttgaacag 360
cggtatcttc ggaatgtatc gcccgcggaa attgcagagg aactcggaat gacggtacag 420
gatgtcgtgt caacaatgaa tgaaggtttt tttgcaaatc tgctgtcaat tgatgaaaag 480
ctccatgatc aagatgacgg ggaaaacatt caagtcatga tcagagatga caaaaatgtt 540
ccgcctgaag aaaagattat gaaggatgaa ctgattgcac agcttgcgga aaaaattcac 600
gaactctctg aaaaagaaca gctggttgtc agtttgttct acaaagagga gttgacactg 660
acagaaatcg gacaagtatt aaatctttct acgtcccgca tatctcagat ccattcaaag 720
gcattattta aattaaagaa tctgctggaa aaagtgatac aataa 765

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctggcgttac ccaacttaat c 21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cttggcgtaa tcatggtcat ag 22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gaggaaacag gtgtggaaga ag 22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ggtcatcttc tgtctgcgtg 20

<210> SEQ ID NO 17
<211> LENGTH: 1650
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
ctatgaccat gattacgcca agtgaataat gagaaacagt caaagaaaaa gaaaacagaa 60
cgcctgctgt cagagtgcat ttttgataca aaaaataatt cagcagaagg tatgaatatc 120
attttaatag acgatcttta tacaacaggc gccaccttgc acttcgcagc ccgctgctta 180
ttagaaaaag gaaaagccgc ttcagtgtca tcttttacct tgatcagaag ctaaatgatt 240
ctgtttttat gccgatataa tcactagaaa ttgacacagg catattatct aataaggaga 300
aaaaaagatg ggagaactgg ctaattgtcc gaaatgcaat gctttatttt taaaaacaaa 360

```
gctgcaaacc gtatgtcagg cgtgtattaa ggaagaagaa aaatcatttg agactgtcta    420
taaattttta agaaaacagg aaaaccggca atcaactttg agccggataa ctgaggaaac    480
aggtgtggaa gaagagctga tattgaaatt catcaggcag aagcgaattc agatcactca    540
tcttcctaat ttggcatacc cttgtgaaag gtgcgggaca tcgattagag aaggcaagtt    600
ctgcaaggct tgccagtctg atattaagga tcaaatggat catttgaacc acgaggatgc    660
tctgaaaatc gagaaagaaa atagtaaaaa agacacatac tatgcctata ataccaaaaa    720
cagctgattc cctaaactaa ctgaaaacgc agtcgataaa agggttaaga ttgtttaaag    780
actgcaacgg aaagcgagag gaatcctatg aaaatcaatc aactgcagtt ttataaaaag    840
caataaaaaa ggagaaagcc catgtcagcg aaggcaatta ttgaacaatt gaagcgactt    900
tgcgttctgc atgagcacct gctcacgctg tctgaagaaa agacggaagc gctcaaagcc    960
ggcaaaacaa aagagctttc taacattttg acaaaagagc aaaaatatat tcaagcaatc   1020
acgcagacag aagatgaccg gatcaaaaca acttcggcct ttctcggata tagcgaaaat   1080
aatactattt ccgcatgtat cgccaaaacc tcaggcagtg aaaaggaaga gctggaacaa   1140
ctatacgaat ctctttctca agttctcgga cgtctgaaaa aagtaaatga gatgaatagg   1200
cagctgacaa gagacgcgct gcaattcatc tctatttcgt acgatatgct ggttcctaag   1260
gaaaataact tcaattacag caaatcaatt aaagctgagc tgccgaaaag tagcaaaatg   1320
aaactgtttg attcaaaagc ttagcagaaa ggaattcaga aaatgacatc tacctttatg   1380
gggcttgaaa ctgcaaggcg ggcgttaagc gctcagcagg cagcgttaag cactactgca   1440
aataacgtgg caaatgccaa tactgatggt tatacaagac agcgggtctc attggaggca   1500
actgactatt tccctgctgt atctaaaaat gcagaaaaaa cagcgggaca aatgggtacg   1560
ggcgttcaag gaaaatcagt tgagagaata agagatatct ttcttgacta ccaataccgt   1620
cttcaaaacc tggcgttacc caacttaatc                                    1650
```

<210> SEQ ID NO 18
<211> LENGTH: 2360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
ctatgaccat gattacgcca agtgaacaat gatcattcat acgaagtacc atggccaaat     60
gaacataaaa gaagaacaaa tcattctttt tgaaagcggg attccaggct ttttagaaga    120
aaaacagttc gtcatacttc cgctttcaga agactctcca ttcgtggcac tgcagtccgt    180
cacttcagaa aatcttgcgt ttatcgtcgt aagtccgttt atcttttttta agaattatga    240
atttgatctt gatgaatcaa ctgctgaact tttggatatc gataatattc aagacgtaga    300
agtcatgaca atattgacta tggcagagcc atttgaaaag tctactgcga atttattggc    360
tcccattatt gtgaatcgca agaacatgat ggctaagcaa gtcgttttac acgactcctc    420
atatacgaca aagcatccga ttggaggaga atcatgctag ttttatcgcg gaaaataaac    480
gaagcgattc aaataggtgc tgatattgaa gtaaaagtga ttgcggttga aggggatcaa    540
gtgaagcttg gaattgacgc cccaaagcat attgatattc acaggaaaga aatttacttg    600
accattcagg aagaaaataa ccgtgcagca gcgttatcca gcgatgtgat ctccgcatta    660
tcctcacaaa aaaagtgagg atttttttat ttttgtatta acaaaatcag agacaatccg    720
```

```
atattaatga tgtagccggg aggaggcgca aaagactcag ccagttacaa aataagggca    780
caagaacgtg ccttaacaac atattcaggg aggaacaaaa caatgcgtaa aggagaagaa    840
cttttcactg gagttgtccc aattcttgtt gaattagatg gtgatgttaa tgggcacaaa    900
ttttctgtca gtggagaggg tgaaggtgat gcaacatacg gaaaacttac ccttaaattt    960
atttgcacta ctggaaaact acctgttcca tggccaacac ttgtcactac tttcggttat   1020
ggtgttcaat gctttgcgag atacccagat catatgaaac ggcatgactt tttcaagagt   1080
gccatgcccg aaggttatgt acaggaaaga actatatttt tcaaagatga cgggaactac   1140
aagacacgtg ctgaagtcaa gtttgaaggt gatacccttg ttaatagaat cgagttaaaa   1200
ggtattgatt ttaaagaaga tggaaacatt cttggacaca aattggaata caactataac   1260
tcacacaatg tatacatcat ggcagacaaa caaaagaatg gaatcaaagt taacttcaaa   1320
attagacaca acattgaaga tggaagcgtt caactagcag accattatca acaaaatact   1380
ccaattggcg atggccctgt ccttttacca gacaaccatt acctgtccac acaatctgcc   1440
ctttcgaaag atcccaacga aaagagagac cacatggtcc ttcttgagtt tgtaacagct   1500
gctgggatta cacatggcat ggatgaacta tacaaataat tttaaaaaag accttggcgt   1560
tgccagggtc ttttaattta aatttctatc tcctaatcat tcctcatcct gtcactaact   1620
catgatataa taaccggatt ctccactaac tttttataaa tgtatttcca tacaagaaat   1680
ctaaaacaga agattttttt ccaaaaatat gtgtaatctt atctcgactt agtcgatata   1740
aacgatagat tggggcatag gggatgatca attgaacatt gaaaggctca ctacgttaca   1800
acctgtttgg gatcgttatg atactcaaat acataatcag aaagataatg ataacgaggt   1860
tcctgttcat caagtttcat ataccaatct tgctgaaatg gtgggggaaa tgaacaagct   1920
tttggaacct tcgcaagttc atctgaagtt cgagcttcat gacaagttaa atgaatacta   1980
tgtaaaggta atagaggact ctacaaatga agtgatccgc gaaattccac caaaacggtg   2040
gcttgatttt tatgcggcta tgactgaatt tcttgggtta tttgtagatg aaaaaaagta   2100
gaataggagt ggtttgagat ggtcacaaga ataacaggtc tggcgtcagg aatggatata   2160
gatgatatcg tatcaaagct gatgcagaca gaaagagcgc cgcttgataa gctgacacaa   2220
aaaaagcaga ctcttgaatg gcagcgtgac agctatcgtg aagtaaactc aaaaataaaa   2280
gaattgcaag attatatgtc taaaaatacg ttgacatatc cgagcacgta tcagagcaac   2340
tggcgttacc caacttaatc                                                2360
```

<210> SEQ ID NO 19
<211> LENGTH: 3164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
ctatgaccat gattacgcca agtgaacaat gatcattcat acgaagtacc atggccaaat     60
gaacataaaa gaagaacaaa tcattctttt tgaaagcggg attccaggct tttagaaga    120
aaaacagttc gtcatacttc cgctttcaga agactctcca ttcgtggcac tgcagtccgt    180
cacttcagaa aatcttgcgt ttatcgtcgt aagtccgttt atcttttta agaattatga    240
atttgatctt gatgaatcaa ctgctgaact tttggatatc gataatattc aagacgtaga    300
agtcatgaca atattgacta tggcagagcc atttgaaaag tctactgcga atttattggc    360
```

```
tcccattatt gtgaatcgca agaacatgat ggctaagcaa gtcgttttac acgactcctc    420
atatacgaca aagcatccga ttggaggaga atcatgctag ttttatcgcg gaaaataaac    480
gaagcgattc aaataggtgc tgatattgaa gtaaaagtga ttgcggttga aggggatcaa    540
gtgaagcttg gaattgacgc cccaaagcat attgatattc acaggaaaga aatttacttg    600
accattcagg aagaaaataa ccgtgcagca gcgttatcca gcgatgtgat ctccgcatta    660
tcctcacaaa aaaagtgagg atttttttat ttttgtatta acaaaatcag agacaatccg    720
atattaatga tgtagccggg aggaggcgca aaagactcag ccagttacaa aataagggca    780
caagaacgtg ccttaacaac atattcaggg aggaacaaaa caatgaatat ggctgaaatc    840
gcccagcttg gagtctcaaa cccgtacaaa caacagtacg aaaactatat tggcggagct    900
tgggttccgc cggccggtgg cgaatacttt gaatctacaa cgccgattac gggaaaacct    960
tttacaagag ttccgcgctc cggccaacag gatgtggacg cagcgttaga tgctgcccat   1020
gcagcgaaag ctgcctgggc tagaacatca acaacggaac gcgccaatat tttaaaccgc   1080
atcgcagatc gtattgaagc gaatttgaaa ctgcttgctg tcgccgaaag cattgacaac   1140
ggaaaacctg taagagaaac aacggcagcg gatctgccgc ttgcagtgga ccattttcgt   1200
tattttgcag gttgcatcag agcacaagaa ggcggcatta gcgaaatcga tgcagacaca   1260
attgcgtacc attttcatga acctctgggt gttgtgggcc agattatccc gtggaatttt   1320
cctttattga tggcgacgtg gaaactggca ccggcgcttg ctgccggaaa ctgtgtcgta   1380
cttaaacctg cagaacaaac accggcgtct atcttagttt tgatggaagt gattggcgat   1440
ctgctgccgc cgggcgttgt gaatgtcatc aacggttttg gcttagaagc tggcaaacct   1500
ttggcctcaa gcccgcgtat ttccaaagta gcttttacgg gtgaaacaac gacaggccgg   1560
ttaatcatgc aatatgcatc acagaatttg attcctgtta cactggaact tggcggaaaa   1620
agcccgaaca ttttctttga agatgtgtta gcagcggatg acgcattttt cgacaaagcg   1680
ctggaaggat ttgcaatgtt tgcgcttaat caaggcgaag tttgcacatg tccttcacgt   1740
gctctgatcc aggaaagcat ttatgatcgg tttatggaaa gagccctgaa acgcgtggct   1800
gccatcagac aaggacatcc gcttgacacg ggaacaatga ttggtgctca agcctctgca   1860
gaacagttag aaaaaatctt gtcctacatt gatctgggca gaaaagaagg agcacagtgc   1920
cttacgggtg gcgaacgcaa tgtcctggat ggcgaccttg caggcggcta ttacgtcaaa   1980
cctacagtat ttgcgggaca taacaaaatg cgcatctttc aagaagaaat tttggcccg   2040
gtcgtaagcg ttacgacatt taaagatgaa gaagaagcac tggctatcgc caacgacacg   2100
ttatatggat tgggtgcggg cgtttggaca agagatggag cacgtgcgtt tcggatggga   2160
agaggtattc aagctggccg cgtgtggacg aattgttatc atgcttaccc ggcccatgca   2220
gcgtttggcg gatataaaca gtctggcatc ggacgtgaaa accatcggat gatgttggat   2280
cattaccaac agacaaaaaa tttattggtt tcttactccc cgaacgcgtt gggctttttc   2340
taattttaaa aaagaccttg gcgttgccag ggtcttttaa tttaaatttc tatctcctaa   2400
tcattcctca tcctgtcact aactcatgat ataataaccg gattctccac taacttttta   2460
taaatgtatt tccatacaag aaatctaaaa cagaagattt ttttccaaaa atatgtgtaa   2520
tcttatctcg acttagtcga tataaacgat agattggggc atagggggatg atcaattgaa  2580
cattgaaagg ctcactacgt tacaacctgt ttgggatcgt tatgatactc aaatacataa   2640
tcagaaagat aatgataacg aggttcctgt tcatcaagtt tcatatacca atcttgctga   2700
```

aatggtgggg gaaatgaaca agcttttgga accttcgcaa gttcatctga agttcgagct 2760
tcatgacaag ttaaatgaat actatgtaaa ggtaatagag gactctacaa atgaagtgat 2820
ccgcgaaatt ccaccaaaac ggtggcttga tttttatgcg gctatgactg aatttcttgg 2880
gttatttgta gatgaaaaaa agtagaatag gagtggtttg agatggtcac aagaataaca 2940
ggtctggcgt caggaatgga tatagatgat atcgtatcaa agctgatgca gacagaaaga 3000
gcgccgcttg ataagctgac acaaaaaaag cagactcttg aatggcagcg tgacagctat 3060
cgtgaagtaa actcaaaaat aaaagaattg caagattata tgtctaaaaa tacgttgaca 3120
tatccgagca cgtatcagag caactggcgt tacccaactt aatc 3164

<210> SEQ ID NO 20
<211> LENGTH: 3182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
ctatgaccat gattacgcca agtgaacaat gatcattcat acgaagtacc atggccaaat 60
gaacataaaa gaagaacaaa tcattctttt tgaaagcggg attccaggct ttttagaaga 120
aaaacagttc gtcatacttc cgctttcaga agactctcca ttcgtggcac tgcagtccgt 180
cacttcagaa aatcttgcgt ttatcgtcgt aagtccgttt atcttttta agaattatga 240 atttgatctt gatgaatcaa ctgctgaact tttggatatc gataatattc aagacgtaga 300
agtcatgaca atattgacta tggcagagcc atttgaaaag tctactgcga atttattggc 360
tcccattatt gtgaatcgca agaacatgat ggctaagcaa gtcgttttac acgactcctc 420
atatacgaca aagcatccga ttggaggaga atcatgctag ttttatcgcg gaaaataaac 480
gaagcgattc aaataggtgc tgatattgaa gtaaaagtga ttgcggttga aggggatcaa 540
gtgaagcttg gaattgacgc cccaaagcat attgatattc acaggaaaga aatttacttg 600
accattcagg aagaaaataa ccgtgcagca gcgttatcca gcgatgtgat ctccgcatta 660
tcctcacaaa aaaagtgagg atttttttat ttttgtatta acaaaatcag agacaatccg 720
atattaatga tgtagccggg aggaggcgca aaagactcag ccagttacaa aataagggca 780
caagaacgtg ccttaacaac atattcaggg aggaacaaaa caatgaccaa taatccccct 840
tcagcacaga ttaagcccgg cgagtatggt ttcccccctca agttaaaagc ccgctatgac 900
aactttattg gcggcgaatg ggtagcccct gccgacggcg agtattacca gaatctgacg 960
ccggtgaccg ggcagctgct gtgcgaagtg gcgtcttcgg gcaaacgaga catcgatctg 1020
gcgctggatg ctgcgcacaa agtgaaagat aaatgggcgc acacctcggt gcaggatcgt 1080
gcggcgattc tgtttaagat tgccgatcga atggaacaaa acctcgagct gttagcgaca 1140
gctgaaacct gggataacgg caaacccatt cgcgaaacca gtgctgcgga tgtaccgctg 1200
gcgattgacc atttccgcta tttcgcctcg tgtattcggg cgcaggaagg tgggatcagt 1260
gaagttgata gcgaaaccgt ggcctatcat ttccatgaac cgttaggcgt ggtggggcag 1320
attatcccgt ggaacttccc gctgctgatg gcgagctgga aaatggctcc cgcgctggcg 1380
gcgggcaact gtgtggtgct gaaacccgca cgtcttaccc cgctttctgt actgctgcta 1440
atggaaattg tcggtgattt actgccgccg ggcgtggtga acgtggtcaa tggcgcaggt 1500
ggggtaattg gcgaatatct ggcgacctcg aaacgcatcg ccaaagtggc gtttaccggc 1560

```
tcaacggaag tgggccaaca aattatgcaa tacgcaacgc aaaacattat tccggtgacg   1620

ctggagttgg gcggtaagtc gccaaatatc ttctttgctg atgtgatgga tgaagaagat   1680

gcctttttcg ataaagcgct ggaaggcttt gcactgtttg cctttaacca gggcgaagtt   1740

tgcacctgtc cgagtcgtgc tttagtgcag gaatctatct acgaacgctt tatggaacgc   1800

gccatccgcc gtgtcgaaag cattcgtagc ggtaacccgc tcgacagcgt gacgcaaatg   1860

ggcgcgcagg tttctcacgg gcaactggaa accatcctca actacattga tatcggtaaa   1920

aaagagggcg ctgacgtgct cacaggcggg cggcgcaagc tgctggaagg tgaactgaaa   1980

gacggctact acctcgaacc gacgattctg tttggtcaga acaatatgcg ggtgttccag   2040

gaggagattt ttggcccggt gctggcggtg accaccttca aaacgatgga agaagcgctg   2100

gagctggcga acgatacgca atatggcctg ggcgcgggcg tctggagccg caacggtaat   2160

ctggcctata agatggggcg cggcatacag gctgggcgcg tgtggaccaa ctgttatcac   2220

gcttacccgg cacatgcggc gtttggtggc tacaaacaat caggtatcgg tcgcgaaacc   2280

cacaagatga tgctggagca ttaccagcaa accaagtgcc tgctggtgag ctactcggat   2340

aaaccgttgg ggctgttcta attttaaaaa agaccttggc gttgccaggg tcttttaatt   2400

taaatttcta tctcctaatc attcctcatc ctgtcactaa ctcatgatat aataaccgga   2460

ttctccacta actttttata aatgtatttc catacaagaa atctaaaaca gaagattttt   2520

ttccaaaaat atgtgtaatc ttatctcgac ttagtcgata taaacgatag attggggcat   2580

aggggatgat caattgaaca ttgaaaggct cactacgtta caacctgttt gggatcgtta   2640

tgatactcaa atacataatc agaaagataa tgataacgag gttcctgttc atcaagtttc   2700

atataccaat cttgctgaaa tggtggggga aatgaacaag cttttggaac cttcgcaagt   2760

tcatctgaag ttcgagcttc atgacaagtt aaatgaatac tatgtaaagg taatagagga   2820

ctctacaaat gaagtgatcc gcgaaattcc accaaaacgg tggcttgatt tttatgcggc   2880

tatgactgaa tttcttgggt tatttgtaga tgaaaaaaag tagaatagga gtggtttgag   2940

atggtcacaa gaataacagg tctggcgtca ggaatggata tagatgatat cgtatcaaag   3000

ctgatgcaga cagaaagagc gccgcttgat aagctgacac aaaaaaagca gactcttgaa   3060

tggcagcgtg acagctatcg tgaagtaaac tcaaaaataa aagaattgca agattatatg   3120

tctaaaaata cgttgacata tccgagcacg tatcagagca actggcgtta cccaacttaa   3180

tc                                                                  3182
```

<210> SEQ ID NO 21
<211> LENGTH: 76
<212> TYPE: RNA
<213> ORGANISM: Bacillus subtilis

<400> SEQUENCE: 21

```
uauaacacca auuaagagua acaaaacaag gagggacuua uacaacaauu ccgugcagga     60

acacgggaau aaaaca                                                     76
```

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 22

-continued

```
His His His His His His
1               5
```